(12) United States Patent
Acharya et al.

(10) Patent No.: US 7,144,989 B2
(45) Date of Patent: Dec. 5, 2006

(54) PEGYLATED NON-HYPERTENSIVE HEMOGLOBINS, METHODS OF PREPARING SAME, AND USES THEREOF

(75) Inventors: Seetharama A. Acharya, Cresskill, NJ (US); Paul K. Smith, Roscoe, IL (US); Belur N. Manjula, Cresskill, NJ (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 158 days.

(21) Appl. No.: 10/957,200

(22) Filed: Oct. 1, 2004

(65) Prior Publication Data

US 2005/0159339 A1    Jul. 21, 2005

Related U.S. Application Data

(60) Continuation-in-part of application No. 10/741,767, filed on Dec. 19, 2003, now Pat. No. 6,962,954, which is a division of application No. 10/105,644, filed on Mar. 25, 2002, now Pat. No. 6,737,524.

(60) Provisional application No. 60/564,705, filed on Apr. 23, 2004.

(51) Int. Cl.
*A61K 38/42* (2006.01)
*C07K 14/805* (2006.01)
*C07K 1/00* (2006.01)

(52) U.S. Cl. .................... 530/385; 514/6; 530/350
(58) Field of Classification Search ............... 530/385, 530/350; 514/6
See application file for complete search history.

(56) References Cited

U.S. PATENT DOCUMENTS

| | | | |
|---|---|---|---|
| 4,220,717 A | 9/1980 | Kuo | |
| 4,356,170 A | 10/1982 | Jennings et al. | |
| 5,349,052 A | 9/1994 | Delgado et al. | |
| 5,585,468 A | 12/1996 | Coughlin et al. | |
| 5,585,484 A | 12/1996 | Acharya et al. | |
| 5,750,725 A | 5/1998 | Acharya et al. | |
| 5,880,255 A | 3/1999 | Delgado et al. | |
| 6,017,943 A | 1/2000 | Acharya et al. | |
| 6,312,916 B1 | 11/2001 | Kopetzki et al. | |
| 6,737,524 B1 | 5/2004 | Smith | |
| 6,962,954 B1 | 11/2005 | Smith | |
| 7,019,117 B1 | 3/2006 | Acharya et al. | |
| 2004/0002443 A1 | 1/2004 | Acharya et al. | |
| 2005/0201988 A1 | 9/2005 | Acharya et al. | |

FOREIGN PATENT DOCUMENTS

| | | |
|---|---|---|
| EP | 0 126 043 A1 | 11/1984 |
| EP | 0 157 899 A2 | 10/1985 |
| EP | 0 126 043 B1 | 10/1989 |
| EP | 0 157 899 B1 | 6/1992 |
| WO | WO 03/008932 | 12/2003 |
| WO | WO 2004/058291 | 7/2004 |

OTHER PUBLICATIONS

Kricheldorf et al. Chemical Abstracts, 95:25583, 1981.
Viswanathan et al., Indian Journal of Chemistry, 20B, 308-310, 1981.
Squires, Jerry E., "Artificial Blood," Science, 295:1002, 1004-1005 (Feb. 8, 2000).
Harris, J. Milton, ed., Poly(ethylene Glycol) Chemistry: Biotechnical and Biomedical Applications: Topics in Applied Chemistry, Plenum Press (New York: 1992), pp. 1-379.
Harris, J. Milton and Samuel Zalipsky, eds., Poly(ethylene Glycol) Chemistry and Biological Applications: ACS Symposium Series 680, American Chemical Society Publishing (Washington, D.C.: 1977), p. 1-341.
Shearwater Corporation, Catalog 2001: Polyethylene Glycol and Derivatives for Biomedical Applications, Huntsville, AL 35801, pp. 1-17.
Budavari, Susan et al., eds, Merck Index, 11th Ed., Merck & Co., Inc. (Rahway, N.J.: 1989), p. 7275, Compound No. 7268.
Porro et al., "Specific Antibodies to Diphtheria Toxin and Type 6A Pneumococcal Capsular Polysaccharide Induced By a Model of Semi-Synthetic Glycoconjugate Antigen," 1985, Mol. Immunol., 22:907-919.
Anderson et al., "Vaccines Consisting of Periodate-Cleaved Oligosaccharides from the Capsule of Haemophilus Influenze Type b Coupled to a Protein Carrier: Structural and Temporal Requirements for Priming in the Human Infant," 1986, J. Immunol., 137:1181-1186.
Witte et al., "Enzymatic Glycoprotein Synthesis: Preparation of Ribonuclease Glycoforms via Enzymatic Glycopeptide Condensation and Glycosylation," (1997) J. Am. Chem. Soc., 119:2114-2118.

(Continued)

*Primary Examiner*—Jon Weber
*Assistant Examiner*—Robert B. Mondesi
(74) *Attorney, Agent, or Firm*—Amster, Rothstein & Ebenstein LLP

(57) ABSTRACT

The present invention provides pegylated hemoglobins comprising a thiocarbamoyl-phenyl-polyethylene glycol (PEG) attached to hemoglobin, and comprising a polyethylene glycol (PEG) attached to hemoglobin by an acyl group. The invention also provides methods of preparing pegylated hemoglobins using isothiocyanato phenyl carbamate of PEG and using isothiocyanato phenyl di-PEG carbamate. The invention further provides compositions and blood substitutes comprising pegylated hemoglobins and methods of treating a subject which comprise administering to the subject blood substitutes comprising non-hypertensive pegylated hemoglobins.

13 Claims, 20 Drawing Sheets

OTHER PUBLICATIONS

Annunziato, Michael E. et al., "p-Maleimidophenyl Isocyanate: A Novel Heterobifunctional Linker for Hydroxyl to Thiol Coupling," Bioconjugate Chem., 4:212-218 (1993).

Aldrich, Aldrich: Catalog Handbook of Fine Chemicals, (1998-1999), p. 83, Product No. 18,627-9.

Manjula, Belur N. et al., "Cys-93-beta-beta Succinimidophenyl Polyethylene Glycol 2600 Hemoglobin A: (Intramolecular Cross-Bridging of Hemoglobin Outside the Central Cavity," J. Biol. Chem., 275(8): 5527-5534 (2000).

Polymase Pharmaceuticals, PLC, "Attachment of Polyethylene Glycol (PEG)," taken from www.polymase.com/PEG/htm (Feb. 8, 2000).

Reaction of Protein Amino Groups with PEG - Isothiocyanate

PEGYLATED NON-HYPERTENSIVE HEMOGLOBINS, METHODS OF PREPARING SAME, AND USES THEREOF

CROSS-REFERENCE TO RELATED APPLICATIONS

This application both claims priority of U.S. Provisional Patent Application No. 60/564,705, filed Apr. 23, 2004, and claims priority of and is a continuation-in-part of U.S. patent application Ser. No. 10/741,767, filed Dec. 19, 2003 now U.S. Pat. No. 6,962,954, which claims priority and is a divisional of U.S. patent application Ser. No. 10/105,644, filed Mar. 25, 2002, now U.S. Pat. No. 6,737,524 B2, issued May 18, 2004, the contents of all of which are hereby incorporated by reference into the subject application.

STATEMENT OF GOVERNMENT SUPPORT

This invention was made with United States government support under National Institutes of Health (NIH) grant numbers HL58247 and HL71064, USPHS NIH Bioengineering Partnership grant 1R24 HL 64395, and U.S. Army grant PR023085. Accordingly, the United States government has certain rights in this invention.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

The development of blood substitutes as in vivo oxygen-carriers has been one of the major aspects of modern transfusion medicine (1). The limitations of acellular hemoglobin (Hb) to be used as Hb based oxygen carriers, such as low plasma retention time, and the high oxygen affinity (relative to that of erythrocytes) were addressed in the design of the first generation of blood substitute products. The preclinical and clinical investigations of the first generation products have identified the vasoconstrictive (hypertension) activity of acellular Hb (inducing a 'pressor' effect) as the major toxicity of the first generation products (2–8). Accordingly, intense efforts have been directed over the years to overcome this limitation and/or the toxicities of acellular Hb by chemical modification of hemoglobin or by a combination of site directed mutagenesis and chemical modification (9–18).

The intrinsic high affinity of Hb for nitric oxide (NO) (a vasodilator) has been advanced as the molecular basis for the vasoconstrictive activity of acellular Hb. Enhancing the molecular size of Hb by oligomerization (inter molecular cross-linking) and protein engineering the heme pockets of Hb by site directed mutagenesis to reduce the affinity of heme to NO have been the two major approaches that have been advanced as ways to overcome the vasoactivity of Hb.

Polyethylene glycol (PEG) chains have been used to modify Hb. The observation that PEGylated bovine Hb carrying ten copies of PEG-5000 linked to the surface amino groups of Hb through isopeptide linkage is vasoinactive, even though it has nearly the same affinity to NO as the parent Hb has suggested PEGylation of Hb is another approach to overcome or modulate the vasoactivity of acellular Hb without engineering the affinity of Hb to nitric oxide (16–18). The calculated molecular weight of this PEGylated bovine Hb is 104,000 kDa, and colligative properties (viscosity and colloidal oncotic pressure) of solutions of this PEGylated bovine are considerably higher than that of unmodified Hb. Accordingly, endowing Hb solutions with high viscosity and high oncotic pressure appeared to be a potential approach to overcome the hypertensive activity of acellular Hb. The molecular radius of the PEGylated bovine Hb is also higher than unmodifed Hb suggesting that the size enhancement of the Hb molecule that accompanies PEGylation may be another factor that has resulted in the neutralization of the vasoactivity of Hb. A polymeric form of ββ-sebacyl Hb with a molecular radius higher than 25 nm has also been shown to be non-hypertensive. Thus, the size enhancement that is accompanied by inducing high viscosity and colloidal oncotic pressure to Hb appears to be a potential new approach to overcome the vasoactivity without interfering with the NO binding activity of Hb.

SUMMARY OF THE INVENTION

The present invention provides a PEGylated hemoglobin comprising a thiocarbamoyl-phenyl-polyethylene glycol (PEG) attached to hemoglobin, and a PEGylated hemoglobin comprising a thiocyanato phenyl 2,4-Di polyethylene glycol (PEG) carbamate conjugated to hemoglobin.

The invention also provides a method of preparing a PEGylated hemoglobin which comprises preparing an isothiocyanato phenyl carbamate of a polyethylene glycol (PEG) and reacting the isothiocyanato phenyl carbamate of a polyethylene glycol (PEG) with hemoglobin to produce a PEGylated hemoglobin, wherein the method of preparing an isothiocyanato phenyl carbamate of a polyethylene glycol (PEG) comprises:

(a) synthesizing 4-carboxy phenyl isothiocyanate from para-amino benzoic acid;

(b) synthesizing 4-isothiocyanato benzoyl azide from 4-carboxy phenyl isothiocyanate;

(c) synthesizing 4-phenyl isothiocyanato isocyanate in situ following thermal decomposition of 4-isothiocyanato benzoyl azide; and (d) reacting 4-phenyl isothiocyanato isocyanate with monomethoxy polyethylene glycol to form an isothiocyanato phenyl carbamate of polyethylene glycol.

The invention provides a method of PEGylating a hemoglobin which comprises reacting isothiocyanato phenyl carbamate of a polyethylene glycol (PEG) with hemoglobin to produce a thiocarbamoyl-phenyl-polyethylene glycol (PEG) attached to the hemoglobin. The invention also provides a method of PEGylating a hemoglobin which comprises reacting a thiocyanato phenyl 2,4-Di-polyethylene glycol (PEG) carbamate with hemoglobin.

The invention also provides a PEGgylated hemoglobin comprising a polyethylene glycol (PEG) attached to hemoglobin by an acyl group.

The invention further provides compositions and blood substitutes comprising PEGylated hemoglobins and methods of treating a subject which comprise administering to the subject any of the PEGylated hemoglobins or blood substitutes disclosed herein or any PEGylated hemoglobin or blood substitute prepared by any of the methods disclosed herein.

Additional objects of the invention will be apparent from the description which follows.

DETAILED DESCRIPTION OF THE INVENTION

The present invention is directed to PEGylated hemoglobins, methods of preparing the PEGylated hemoglobins, and uses of the PEGylated hemoglobins, where preferably the PEGylated hemoglobins are non-hypertensive. As used herein, "PEGylation" means linking to polyethylene glycol (PEG), and a "PEGylated" hemoglobin is a hemoglobin that has PEG conjugated to it.

Figure 1:
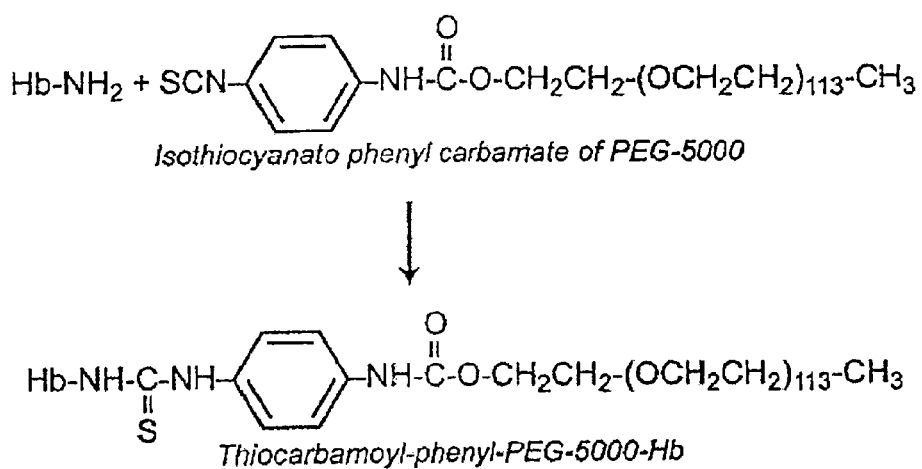
FIG. 1. Schematic representation of the reaction of the isothiocyanato phenyl cabamate of PEG-5000 with the amino groups of Hb.

The invention provides a PEGylated hemoglobin comprising a thiocarbamoyl-phenyl-polyethylene glycol (PEG) attached to hemoglobin. The thiocarbamoyl-phenyl-polyethylene glycol (PEG) can be attached, for example, to an α-amino group or to an ε-amino group of the hemoglobin. The PEGylated hemoglobin can comprise a PEG with a molecular weight of 200–40,000 daltons. Preferably, the polyethylene glycol (PEG) has a molecular weight of 3,000–5,000 daltons, and more preferably 5,000 daltons. Preferably, the PEGylated hemoglobin has two to eight (e.g., 2, 4, 6, or 8) thiocarbamoyl-phenyl-polyethylene glycol (PEG) groups attached to the hemoglobin. More preferably, six thiocarbamoyl-phenyl-polyethylene glycol (PEG) groups are attached to the hemoglobin. PEGylated hemoglobin of the present invention comprises the structures shown in the bottom of FIG. 1 and in the bottom of FIG. 17.

The invention provides a PEGylated hemoglobin comprising a thiocyanato phenyl 2,4-Di polyethylene glycol (PEG) carbamate attached to hemoglobin. The thiocyanato phenyl 2,4-Di polyethylene glycol (PEG) can be attached, for example, to an α-amino group or to an ε-amino group of the hemoglobin. The PEGylated hemoglobin can comprise a PEG with a molecular weight of 200–40,000 daltons. Preferably, the polyethylene glycol (PEG) has a molecular weight of 3,000–5,000 daltons, and more preferably 5,000 daltons. Preferably, two to eight (e.g., 2, 4, 6, or 8) thiocyanato phenyl 2,4-Di polyethylene glycol (PEG) groups are attached to the hemoglobin. More preferably, six thiocyanato phenyl 2,4-Di polyethylene glycol (PEG) groups are attached to the hemoglobin.

Preferably, PEGylated hemoglobins comprising a thiocarbamoyl-phenyl-polyethylene glycol (PEG) or a thiocyanato phenyl 2,4-Di polyethylene glycol (PEG) carbamate have a radius of at least 5 nm. Preferably, these PEGylated hemoglobins have a viscosity of at least 3 cp, i.e. a viscosity that is at least 3 times greater than the viscosity of non-PEGylated hemoglobin. Preferably, these PEGylated hemoglobins have a colloidal osmotic pressure that is greater than the colloidal osmotic pressure of non-PEGylated hemoglobin. Preferably, the colloidal osmotic pressure of the PEGylated hemoglobins is at least 4 to 12 (e.g., 4, 6, 8, 10 or 12) times greater than non-PEGylated hemoglobin.

Monomethyl PEGs of various molecular weights for use in PEGylating hemoglobin can be obtained commercially, for example from Nektar Therapeutics, CA.

The invention also provides an isothiocyanato phenyl carbamate of a polyethylene glycol (PEG). The PEG can have a molecular weight of 200–40,000 daltons. Preferably, PEG has a molecular weight of 3,000–5,000 daltons (e.g., 3,000, 4,000 or 5,000 daltons). The isothiocyanato phenyl carbamate of polyethylene glycol (PEG) of the present invention can have the structure shown in the upper part of FIG. 1.

The invention further provides a method of preparing an isothiocyanato phenyl carbamate of a polyethylene glycol (PEG) comprising:

(a) synthesizing 4-carboxy phenyl isothiocyanate from para-amino benzoic acid;

(b) synthesizing 4-isothiocyanato benzoyl azide from 4-carboxy phenyl isothiocyanate;

(c) synthesizing 4-phenyl isothiocyanato isocyanate in situ following thermal decomposition of 4-isothiocyanato benzoyl azide; and (d) reacting 4-phenyl isothiocyanato isocyanate with monomethoxy polyethylene glycol to form an isothiocyanato phenyl carbamate of polyethylene glycol.

Preferably, step (a) of the method is carried out in the presence of sodium acetate and $CSCl_2$. Preferably, step (b) is carried out in the presence of methylene chloride, pyridine, phenyl dichlorophosphate, and sodium azide. The PEG can have a molecular weight of 200–40,000 daltons. Preferably, PEG has a molecular weight of 3,000–5,000 (e.g., 3,000, 4,000 or 5,000) daltons. Also provided is an isothiocyanato phenyl carbamate of a polyethylene glycol (PEG) prepared by any of the methods disclosed herein.

The invention provides a method of pegylating a hemoglobin which comprises reacting any of the isothiocyanato phenyl carbamate of a polyethylene glycol (PEG) disclosed herein with hemoglobin to produce a thiocarbamoyl-phenyl-polyethylene glycol (PEG) attached to the hemoglobin. Also provided is a PEGylated hemoglobin prepared by this method. The PEGylated hemoglobin comprises a thiocarbamoyl-phenyl-polyethylene glycol (PEG) attached to an α-amino group and/or to an ε-amino group of the hemoglobin. The PEGylated hemoglobin can comprise a PEG with a molecular weight of 200–40,000 daltons. Preferably, the polyethylene glycol (PEG) has a molecular weight of 3,000–5,000 (e.g., 3,000, 4,000 or 5,000) daltons. Preferably, the PEGylated hemoglobin has two to eight (e.g., 2, 4, 6 or 8) thiocarbamoyl-phenyl-polyethylene glycol (PEG) groups attached to the hemoglobin. More preferably, six thiocarbamoyl-phenyl-polyethylene glycol (PEG) groups are attached to the hemoglobin. PEGylated hemoglobin of the present invention comprises the structures shown in the bottom of FIG. 1 and in the bottom of FIG. 17.

The invention also provides a thiocyanato phenyl 2,4-Dipolyethylene glycol (PEG) carbamate. The PEG can have a molecular weight of 200–40,000 daltons. Preferably, PEG has a molecular weight of 3,000–5,000 (e.g., 3,000, 4,000 or 5,000) daltons. Also provided is a method of PEGylating a hemoglobin which comprises reacting the thiocyanato phenyl 2,4-Di-polyethylene glycol (PEG) carbamate with hemoglobin. Also provided is a PEGylated hemoglobin prepared by this method. The thiocyanato phenyl 2,4-Di polyethylene glycol (PEG) can be attached, for example, to an α-amino group or to an ε-amino group of the hemoglobin. The pegylated hemoglobin can comprise a PEG with a molecular weight of 200–40,000 daltons. Preferably, the polyethylene glycol (PEG) has a molecular weight of 3,000–5,000 daltons (e.g., 3,000, 4,000 or 5,000 daltons). Preferably, two to eight (e.g., 2, 4, 6 or 8) thiocyanato phenyl 2,4-Di polyethylene glycol (PEG) groups are attached to the hemoglobin. More preferably, six thiocyanato phenyl 2,4-Di polyethylene glycol (PEG) groups are attached to the hemoglobin.

In different embodiments of any of the PEGylated hemoglobins described herein, two to eight (e.g., 2, 4, 6 or 8) PEG groups are attached to the hemoglobin.

Figures 18A, 18B, 18C, 18D:
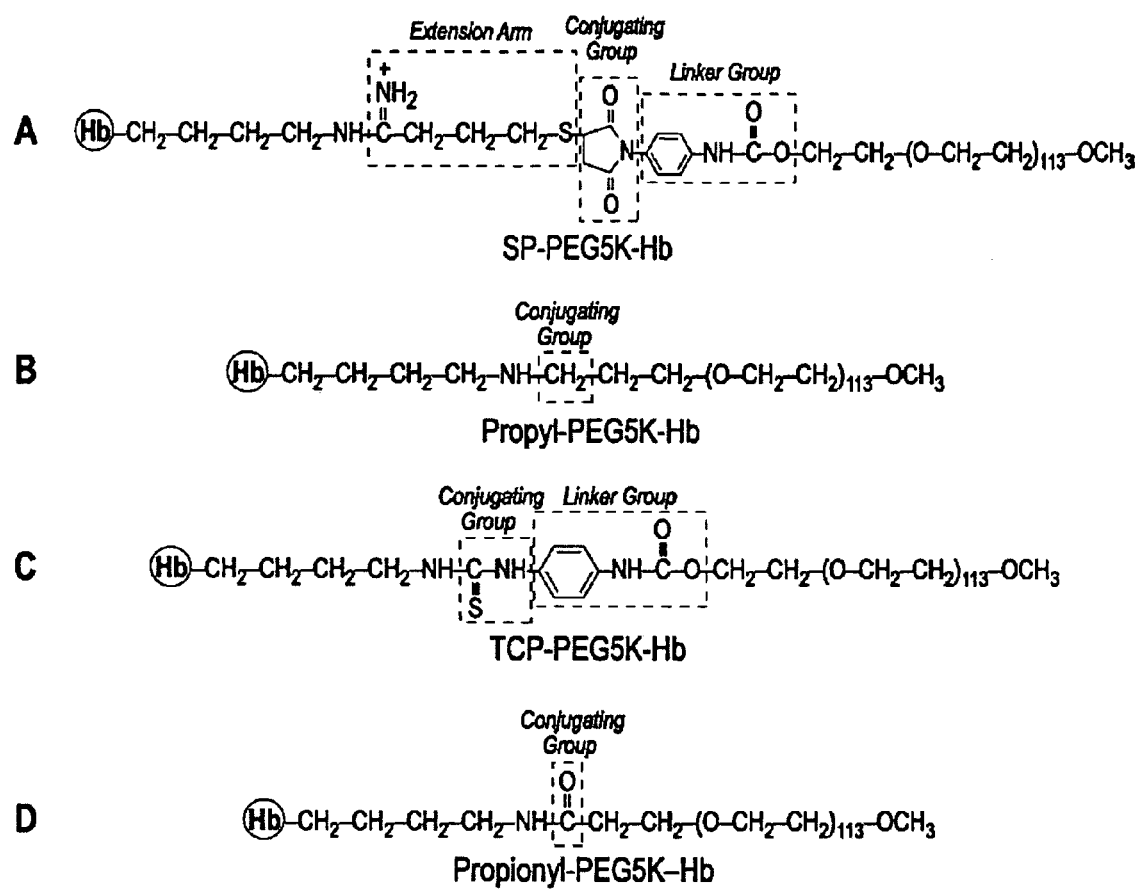
FIG. 18A–18D. Schematic representation of the linkage between PEG and amino groups of Hb in PEGylated Hbs generated by (A) thiolation mediated maleimide chemistry; (B) reductive alkylation chemistry, (C) thiocarbamoylation chemistry and (D) acylation chemistry.

The invention also provides a PEGgylated hemoglobin comprising a polyethylene glycol (PEG) attached to hemoglobin by an acyl group. The polyethylene glycol (PEG) can be attached, for example, via an α-amino group or via an ε-amino group of the hemoglobin. In different embodiments, the PEG can have a molecular weight of 200–40,000 daltons. A preferred PEG has a molecular weight of 3,000–5,000 (e.g., 3,000, 4,000 or 5,000) daltons. In one embodiment, the PEGylated hemoglobin comprises the structure shown in FIG. 18D. Preferably, two to eight (e.g., 2, 4, 6 or 8) polyethylene glycol (PEG) groups are attached to the hemoglobin. More preferably, six polyethylene glycol (PEG) groups are attached to the hemoglobin. Preferably, the PEGylated hemoglobin has a radius of at least 6 nm. Preferably, the PEGylated hemoglobin has a viscosity that is at least 4 to 12 (e.g., 4, 6, 8, 10 or 12) times greater than non-PEGylated hemoglobin.

The invention provides a PEGylated hemoglobin prepared by any of the methods disclosed herein.

The invention also provides a composition comprising any of the PEGylated hemoglobins disclosed herein or prepared by any of the methods disclosed herein, and a pharmaceutically acceptable carrier. The invention further provides a blood substitute comprising any of the PEGylated hemoglobins disclosed herein or prepared by any of the methods disclosed herein. Pharmaceutically acceptable carriers include, but are not limited to, saline, phosphate buffered saline, Ringer's solution, lactated Ringer's solution, Locke-Ringer's solution, Kreb's Ringer's solution, Hartmann's balanced saline solution, and/or heparinized sodium citrate acid dextrose solution. The pharmaceutical compositions also may comprise known plasma substitutes and plasma expanders. The pharmaceutical compositions of the present invention may be used as blood substitutes, and the like, and may be administered by conventional means including but not limited to transfusion and injection.

The invention provides a method of treating a subject which comprises administering to the subject any of the PEGylated hemoglobins or blood substitutes disclosed herein or any PEGylated hemoglobin or blood substitute prepared by any of the methods disclosed herein. Prior to treatment, the subject may have a reduced red blood cell count or a reduced blood volume. The reduced blood volume may be due to a wound or to surgery. The subject may have a disease characterized by vaso-occlusion or impaired blood flow. Such diseases include, but are not limited to, sickle cell disease, myocardial infarction and/or shock. Preferably, the treatment does not produce hypertension in the subject. Preferably, the treatment does not affect arteriolar diameter or venular diameter in the subject. Preferably, the treatment does not increase vascular resistance in the subject. Preferably, the treatment does not affect the subject's heart rate.

The present invention is illustrated in the following Experimental Details section, which is set forth to aid in the understanding of the invention, and should not be construed to limit in any way the scope of the invention as defined in the claims that follow thereafter.

EXPERIMENTAL DETAILS

I. Overview

The paradigms disclosed herein for the design of second generation Hb based oxygen carriers involve: (i) enhanced molecular size, (ii) increased viscosity and colloidal oncotic pressure of a solution of Hb that are comparable or superior to that of blood and (iii) increased oxygen affinity of the Hb.

In an attempt to define the optimum level of PEGylation on Hb, and/or its dependence on the chemistry used to conjugate PEG-chains to Hb that can bring about the neutralization of the vasoactivity of Hb in vivo, a simple protocol was developed for PEGylation of Hb that does not change the net charge on the molecule as a result of PEGylation. The PEGylation protocol was developed based on the high reactivity and selectivity of thiols for modification with maleimides and the ease with which the ε-amino groups of surface lysine (Lys) residues of Hb could be thiolated using iminothiolane, i.e., could be converted to maleimide reactive sites. This protocol, thiolation mediated maleimide chemistry based PEGylation reaction, was used to generate new vasoinactive PEGylated Hb, hexa-succinimidophenyl PEG-5000 [(SP-PEG5K)$_6$-Hb]. The high oxygen affinity, high viscosity and high oncotic pressure of this PEGylated Hb are thought to contribute to the neutralization of the vasoactivity of acellular Hb (19–24).

The PEGylated bovine Hb of Enzon, a non-hypertensive Hb product, carries nearly 10 copies of PEG-5000 chains per tetramer whereas the new non-hypertensive hexa-succinimido phenyl PEG5K Hb carries on an average six copies of PEG5K chains per tetramer. Therefore, it is clear that vaso-inactive Hb can be generated by surface decoration of Hb with less than ten copies of PEG5K chains. Since the conjugation chemistry used for the preparation of hexa succinimido phenyl PEG5K-Hb is distinct from that used for the preparation of PEGylated bovine Hb, the results suggest that the chemistry used for conjugation of PEG-chains to Hb may also play a role in neutralizing the vasoactivity of Hb by PEGylation, particularly in terms of the extent of the PEGylation needed to generate a non-hypertensive Hb. Since the change in chemistry in the conjugation is generally accompanied by a change in the site selectivity of PEGylation as well, the results obtained with hexa succinimidophenyl PEG-5K Hb, may also imply a role played by the site selectivity of the surface decoration of Hb with PEG-chains.

As described herein, PEGylated Hbs were generated using a conjugation chemistry that is distinct from that of the thiolation mediated maleimide chemistry based PEGylation as well as from the active ester chemistry used by Enzon to generate the PEGylated bovine Hb. The reaction of phenyl isothiocyanate, which shows very high site selectivity for α-amino groups and the low pK$_a$ amino groups of proteins (FIG. 1), was chosen to functionalize PEG. In developing the maleimido phenyl PEG reagent, the high efficiency of the reaction of aryl isocyanates with the aliphatic hydroxyl groups was used to generate the carbamate bond (19). This chemistry was used as a modular platform to achieve the functionalization of PEG with the desired functional group in a one step reaction. The same platform has been used now to synthesize isothiocyanato phenyl carbamate of monomethoxy PEG 5000. The reaction of this new PEGylating agent with Hb has been studied, and the reaction conditions have been optimized to generate a product with a hydrodynamic volume comparable to that of (SP-PEG5K)$_6$Hb. The functional properties of this PEGylated Hb, the colligative properties of the solution of this new PEGylated Hb, and the consequences of PEGylation on the 'pressor effect' of Hb have been investigated. The studies have demonstrated that the new hexaPEGylated Hb is non-hypertensive. The properties of the new product have been compared with that of (SP-PEG5K)$_6$-Hb to gain further insight into the molecular basis of vasoinactivation as result of PEGylation. The development of this new product sets the stage for the pre-clinical and clinical evaluation of this product as a Hb based oxygen carrier.

II. Methods and Materials

Figure 2:
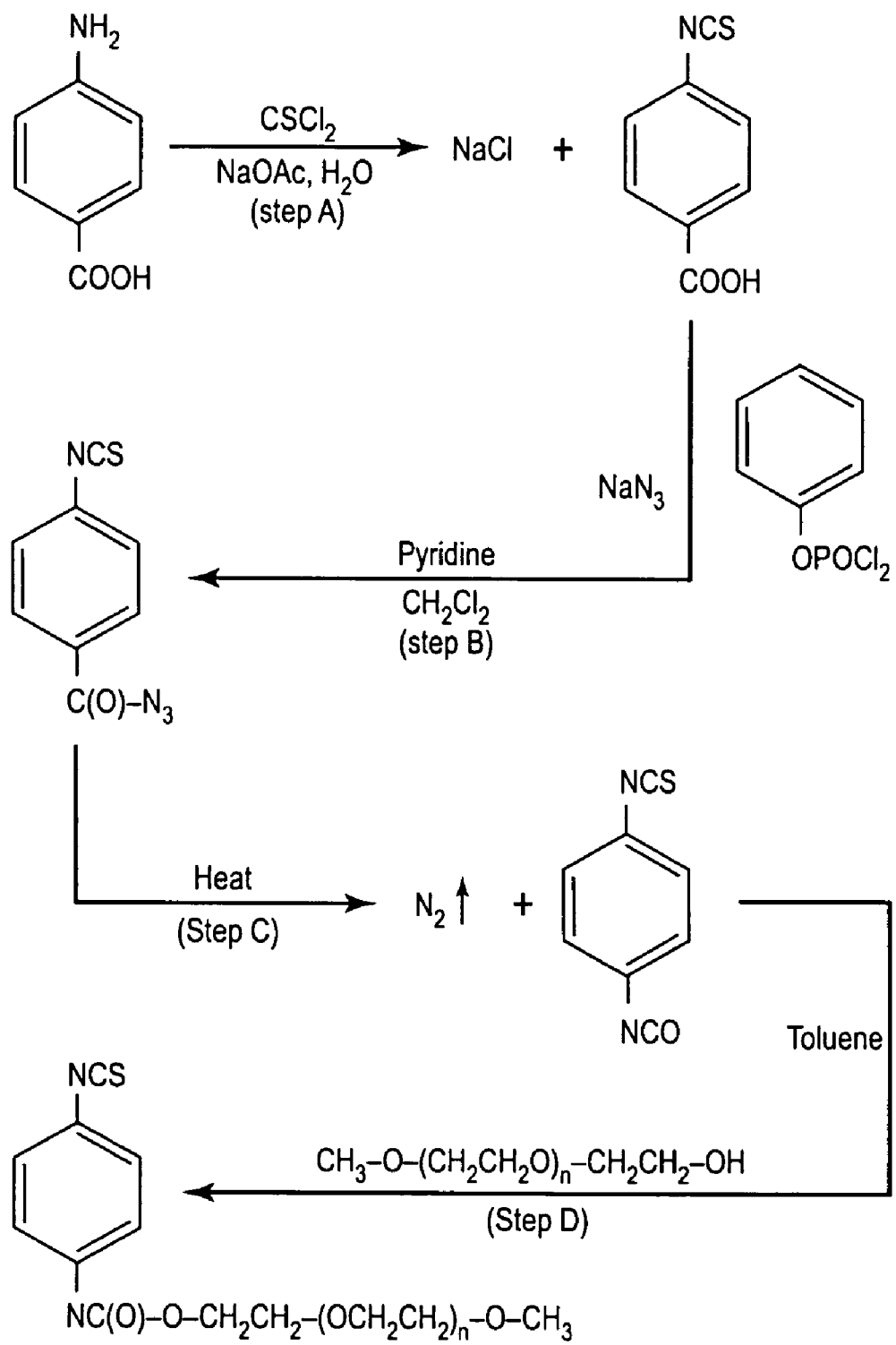
FIG. 2. Schematic representation of the synthesis of isothiocyanato phenyl carbamate of monomethoxy PEG-5000.

Synthesis of isothiocyanato phenyl PEG: The chemical synthesis of phenyl isothiocyanato carbamate of PEG is schematically presented in FIG. 2. The synthesis of the omega methoxy, phenyl thiocyanato PEG has been achieved using the steps described below. The steps of the synthesis of Omega methoxy, phenyl isothiocyanato PEG are (i) synthesis of 4 carboxy phenyl isothiocyanate from paramino benzoic acid; (ii) the conversion of 4-carboxy phenyl isothiocyanate to 4-isothiocyanato benzoyl azide, (iii) the synthesis of 4-phenyl isothiocyanato isocyanate in situ and its reaction with methoxy PEG-5000 to form isothiocyanato phenyl carbamate of PEG-5000.

(i) Synthesis of 4-carboxy phenyl isothiocyanate: Para-aminobenzoic acid (0.2 mole; 26 gms) was dissolved in acetone (400 ml) at room temperature. Activated carbon (about 5 gms, Darco, G60) was added and the mixture was stirred (using magnetic stir bar) for 5 to 10 minutes. The entire solution was filtered yielding a much-lighter colored solution of p-aminobenzoic acid than was initially formed.

Sodium acetate (0.3 moles, 26 gms) was dissolved in about 200 ml of deionized water, and added to the above filtrate of p-aminobenzoic acid, now contained in a 4 liter vacuum flask. A vacuum was applied to the flask with an intermediate dry ice/acetone trap between the flask and the vacuum pump.

Thiophosgene (about 40 gms of neat, red liquid) were added in one portion to the cooled, acetone stripped slurry of p-amino benzoic acid, while stirring rapidly with an overhead paddle stirrer. A tan precipitate formed almost immediately upon the addition of the thiophosgene along with considerable foaming. After the foaming subsided (about 10 minutes), the insoluble precipitate was filtered and dried in vacuo to get a powdery material.

The crude product was crystallized from hot glacial acetic acid to yield yellow needles of 4-carboxy phenyl isothiocyanate (about 16 gms) after drying in a vacuum. Considerable product remained in the mother liquor which was not recovered. The elemental analysis of these crystals is consistent with that of 4-carboxy phenyl isothiocyanate. The crystals darkened but did not melt at 220° C. The infra red spectrum of the crystals was consistent with that expected for 4-carboxy phenyl isothiocyanate.

(ii) Synthesis of 4-Isothiocyanatobenzoyl Azide: Fifteen gms of the 4-carboxyphenyl isothiocyanate was suspended in 200 ml of dry methylene chloride in a one liter side arm vacuum flask along with 16 gms of pyridine (0.2 M), phenyl dichlorophosphate (0.1 M) and 6.5 gms of sodium azide (0.1 M). This mixture was stirred for overnight at room temperature. The stirred mixture was then washed in a separatory funnel with 200 ml of water and then with 200 ml of 0.1 N sulfuric acid. The acid washed methylene chloride layer was dried with anhydrous magnesium sulfate.

The dried methylene chloride reaction solution was evaporated in a rotary evaporator at room temperature (around 20° C.). The resulting light tan crystals were dissolved in minimal amount of ethyl ether at room temperature. The re-crystallization solution was treated with activated carbon (Darco G60) and filtered. The resulting light colored solution was evaporated to dryness at room temperature. White crystals were obtained which melted at 68 to 72° C. with the evolution of nitrogen consistent with azide decomposition. The elemental analysis and infrared spectrum of the crystals confirmed it to be 4-isothiocyanato benzoyl azide. The compound is stable at room temperature but was stored in the freezer.

(iii) Synthesis of 4-isothiocyanatophenyl PEG: The 4-isothiocyanato benzoyl azide was thermally decomposed at about 75°–104° C. (Curtius rearrangement) smoothly and quantitatively as a solution in dry refluxing of a toluene solution to 4-isothiocyanato-phenyl isocyanate. The decomposition reaction was carried out in the presence of monomethoxy polyethylene glycol so that the isocyanate generated in situ reacts with hydroxyl of the momomethoxy PEG.

The monomethoxy polyethylene glycol having a low diol content (manufactured by NOF Corporation, Japan) taken in toluene was stirred and heated to reflux (about 104° C.) and any water present was azeotropically removed. When no more additional water could be removed, the refluxing was discontinued and the contents were cooled under dry nitrogen blanket to about 60° C. To this reaction mixture, p-isothiocyanato benzoyl azide was added and heating was resumed. Nitrogen evolved during the initial 15 to 30 minutes after the heating was resumed. Heating was continued for an additional hour after the evolution of nitrogen ceased, as monitored by the bubble trap at the exit of the condenser. Heating was discontinued and the contents of the flask were allowed to cool to room temperature. The reaction mixture now contains the desired product, m-PEG-5000-O-Carbamoyl phenyl isothiocyanate. The reaction mixture was concentrated under vacuum using a rotary evaporator into a viscous oil. This was treated with anhydrous ethyl ether to induce the crystallization of the activated mPEG-5000. Ethyl ether also extracts the unreacted p-isothiocyanatophenyl isocyanate.

The crude activated mPEG was crystallized out, filtered and dried in vacuum. The dried material was dissolved in water and the water insoluble material was filtered out. The clarified filtrate was extracted with methylene chloride, and the methylene chloride extract that contains the activated mPEG was dried with anhydrous magnesium sulfate and filtered. The filtrate was concentrated under vacuum into a viscous oil and the activated mPEG was recrystallized by the addition of anhydrous ether. The re-crystallized activated mPEG was filtered out and dried under vacuum. The activated material was obtained as a white solid.

The isothiocyanatophenyl PEG chemistry is also described in U.S. patent application Ser. No. 10/105,644, filed Mar. 25, 2002, now U.S. Pat. No. 6,737,524 B2, issued May 18, 2004, the contents of which are hereby incorporated by reference into the subject application.

PEGylation of Hb using isothiocyanato phenyl carbamate of PEG 5K: In a typical PEGylation reaction, oxy Hb (0.5 mM) was incubated with 40 fold excess of activated mPEG-5000 (20mM) in phosphate buffer of desired pH for 6 hr at room temperature or for approximately 18 hrs at 4° C.

The progress of the PEGylation reaction of Hb with isothiocyanato phenyl carbamate of PEG-5K has been monitored by analyzing the reaction mixture after various time intervals of the reaction by size exclusion chromatography on FPLC from Amersham Pharmacia using Superose 12 columns (two Superose 12 analytical columns connected in series was used for this analysis). The enhanced molecular size of Hb that occurs on incubation of Hb with the activated mPEG-5000 demonstrates the modification of Hb by PEG. The various time point aliquots of the reaction mixture were also analyzed by reverse phase HPLC using the conditions used previously to analyze the reaction of maleidophenyl carbamate of PEG5K with HbA.

PEGylation protocol for preparation of $(TC-DiPEG5K)_4$-Hb: The PEG-reagent, ITC-DiPEG5K was synthesized by reaction of 1-thiocyanato, 2,5-dicyanato benzene with omega methoxy PEG-5000. The PEGylation protocol comprised an overnight reaction in Tris-acetate buffer pH 8.5, 0.25 mM in Hb with a 40 fold molar excess (10 fold over α-amino groups) of the reagent. The reaction is quantitative in terms of the modification of HbA, the PEGylated Hb elutes at a position corresponding to that of $(SP-PEG5K)_6$-HbA in FPLC suggesting similar hydrodynamic volume of the two PEGylated Hbs.

Purification of PEG-Hb conjugate: HbA (0.5 mM) was reacted with 20 mM ITP-carbamoylPEG-5K (20mM) in PBS at 4° C. with gentle stirring overnight. The product was then dialyzed in Tris-Acetate buffer, pH 8.5, to remove much of the unreacted ITP-carbamoyl-PEG 5K. The remaining PEG was removed by tangential flow filtration against 15 to 30 volumes with Tris-Acetate buffer pH 8.5 using Minim system from PAL Corporation. A 70k molecular weight cut off membrane was used to filter the PEG reagent from the PEGylated Hb.

The purification of PEG-Hb conjugate generated by the reaction of ITP-carbamoyl-PEG-5K is accomplished by ion-exchange chromatography. Ion exchange chromatography of the PEG-Hb conjugate was carried out on a Q-Sepharose High Performance column (2.6 cm×62 cm) at 4° C. using an AKTA Explorer 10 Protein Purification System (Amersham Biosciences). The column was equilibrated with 50 mM Tris-acetate buffer, pH 8.5. PEG-Hb conjugate was eluted from the column with a decreasing linear pH gradient generated using 50 mM Tris-Ac buffers of pH 8.5 and of pH 7.0 as the starting and final buffers respectively. The effluent was monitored at three wavelengths, 240, 540 and 600 nm.

Preparation of Propionyl PEG5K Hb: PEGylation of HbA with P5K-SPA: Attachment of PEG chains to amino groups of HbA was carried out using succinimidyl-propionate-activated methoxy polyethylene glycol (P5K-SPA, Shearwater Polymers, Huntsville, AB). HbA (0.125, 0.25 and 0.5 mM tetramer) in PBS (pH 7.4) was incubated with 10 mM P5K-SPA, respectively. The reaction mixtures were kept in quiescent condition at 4° C. overnight. Subsequently, the reaction mixtures were dialyzed extensively against PBS (pH 7.4) and then applied for analytical characterization.

For large-scale preparations, the reaction mixture was subjected to diafiltration through a 70-kDa membrane vs. PBS (pH 7.4) using Minim (Pall Corporation, Canada) to remove unreacted PEG and other excess reagent. The retentate was monitored at regular intervals by SEC for the removal of unreactive of PEG. The presence of unreactive PEG in the column effluent was detected by refractive index (RI) measurements online. The final product in the retentate was concentrated and stored frozen at −80° C.

The PEGylated sample generated by the reaction of 0.5 mM Hb with a 10 fold excess of succinimidyl ester of PEG-5000 acid, gave a Product that is isohydrodynamic with non-hypertensive P5K6 molecule that was generated by thiolation mediated maleimide chemistry based PEGylation of Hb.

Analysis of the globin Chains: The $\alpha$- and $\beta$-globin chains of HbA and PEG5K-Hb conjugate were analyzed by RPHPLC using a Vydac C4-column.

Trypsin Digestion: Combined $\alpha$, $\beta$-globins (100 µg) were digested with trypsin (1 µg) in 100 µl ammonium bicarbonate, 100 mM, pH 7.8, at 37° C. for 3 hrs. The peptides were analyzed on a Vydac C18 column using a linear gradient of 5–50% ACN containing 0.1% TFA for 100 mins.

Oxygen affinity measurements: Oxygen equilibrium curves were measured at 37° C. using a Hem-O-Scan (Aminco) in 50 mM BisTris/50 mM Tris Acetate, pH 7.4 and in PBS, pH 7.4 at a Hb tetramer concentration of 0.6 mM.

Molecular radius: The molecular radius of the PEGylated Hbs was determined by dynamic light scattering measurements using an instrument from Protein Solutions, Inc., Model Dynapro MS/X.

Viscosity measurements: The viscosity of the PEGylated Hbs was measured in a cone and plate Rheometer (Brookfield, Middleboro, Mass.), as a function of the concentration of PEGylated Hb, in PBS buffer, pH 7.4 and at 37° C. The instrument was calibrated with deionized water prior to measurements of the viscosity of the Hb samples.

Colloidal osmotic pressure measurements: The colloidal osmotic pressure (COP) of the PEGylated Hbs was determined using a Wescor 4420 Colloidal Osmometer. Measurements were done as a function of the PEGylated Hb concentration, in PBS, pH 7.4 at room temperature. A 30 kDa MW cut-off membrane was used. The instrument was tested with Osmocoll reference standards prior to measurements of the samples.

Vasoactivity of PEGylated Hbs: Analysis of the vasoactivity and microvascular hemodynamics of the PEGylated Hb were carried out in a hamster skin fold window microcirculation model, essentially according to the procedures previously described (27–31). In this model, a chronically implanted dorsal skin fold window is used to quantitatively evaluate the microvascular and systemic conditions in the awake conditions by direct in vivo microscopic observation. Studies were performed on male Golden Syrian Hamsters (Charles Rivers, USA) of 55–70 g body weight. All animal studies were approved by the Animal Subject Committee of University of California, San Diego, and performed according to NIH guidelines for the care and use of laboratory animals (NIH publication #85-23 Rev. 1985).

In these studies, each animal served as its own baseline. Baseline measurements of microvascular vessels and functional capillary density (FCD) were mapped at specific locations identified so the same fields and vessels can be investigated again at a later time point. Mean arterial pressure (MAP), heart rate, arteriolar diameter and FCD were measured at baseline and during the experiment. In top load (hypervolemic) experiments, the animals were infused with a volume of the test solution equivalent to 10% of their blood volume (estimated as 7% of their body weight) (10% hypervolemic infusion) via the jugular vein at a rate of 0.20 ml/min using a microinfusion syringe pump (CMA 100 Microinjection Pump: CMA, Sweden). MAP, heart rate, arteriolar diameter and FCD were measured immediately following the infusion and at 10, 30 and 60 min after the infusion. In extreme hemodilution studies, a progressive, stepwise, isovolemic blood exchange-transfusion (exchange of blood with an equal volume of the chosen solution to maintain the total blood volume) was carried out according to the protocol described previously (29). Briefly, progressive hemodilution to a final systemic hematocrit level of 25% of baseline was accomplished with three isovolemic exchange steps. The first two isovolemic hemodilutions were performed with 6% Dextran-70, a colloid solution, until the systemic hematocrit was reduced to 40% of baseline. The third step was performed with the test solutions, at which stage the systemic hematocrit was reduced to 25% of baseline. The isovolemic exchange transfusion was accomplished by infusion of the choice solution through the jugular vein using a microinfusion syringe pump and simultaneous withdrawal of an equivalent volume of blood from the carotid artery at the same rate.

Microhemodynamic parameters including vessel diameter and functional capillary density were evaluated according to Kerger et al (30). Microvessels in the subcutaneous tissue and the skeletal skin muscle were observed with an inverted microscope and by the trans-illumination technique. Microvessels were classified according to their position within the microvascular network. Arteriolar microvessels were grouped into large feeding arterioles (A1), small arcading arterioles (A2), and transverse arterioles (A3) branching off A1 or A2 vessels and into terminal arterioles (A4). Microvascular diameter was analyzed on-line in arterioles and venules. Vessel diameter was measured with an image-shearing system.

Functional capillary density was analyzed on-line from four to six video-recorded microscopic fields containing four to six different capillaries each. FCD is an indicator of tissue perfusion and the homogeneity of tissue oxygenation (31). Detailed mappings were made of the chamber vasculature so that the same vessels studied at baseline could be followed throughout the experiment. Capillary segments were considered functional if red blood cells (RBCs) were observed to transit over a thirty second period. FCD was tabulated from the capillary lengths with RBC flow in an area comprised of 10 successive microscopic fields (420×320 µm²). Each field had between two and five capillary segments with RBC flow. FCD (cm⁻¹), i.e., total length of RBC perfused capillaries divided by the area of the microscopic field of view, was calculated by measuring and adding the length of capillaries that had RBC transit in the field of view. The relative change in FCD from baseline levels after each intervention is an indicator of the extent of capillary perfusion.

III. Results

Figure 3:
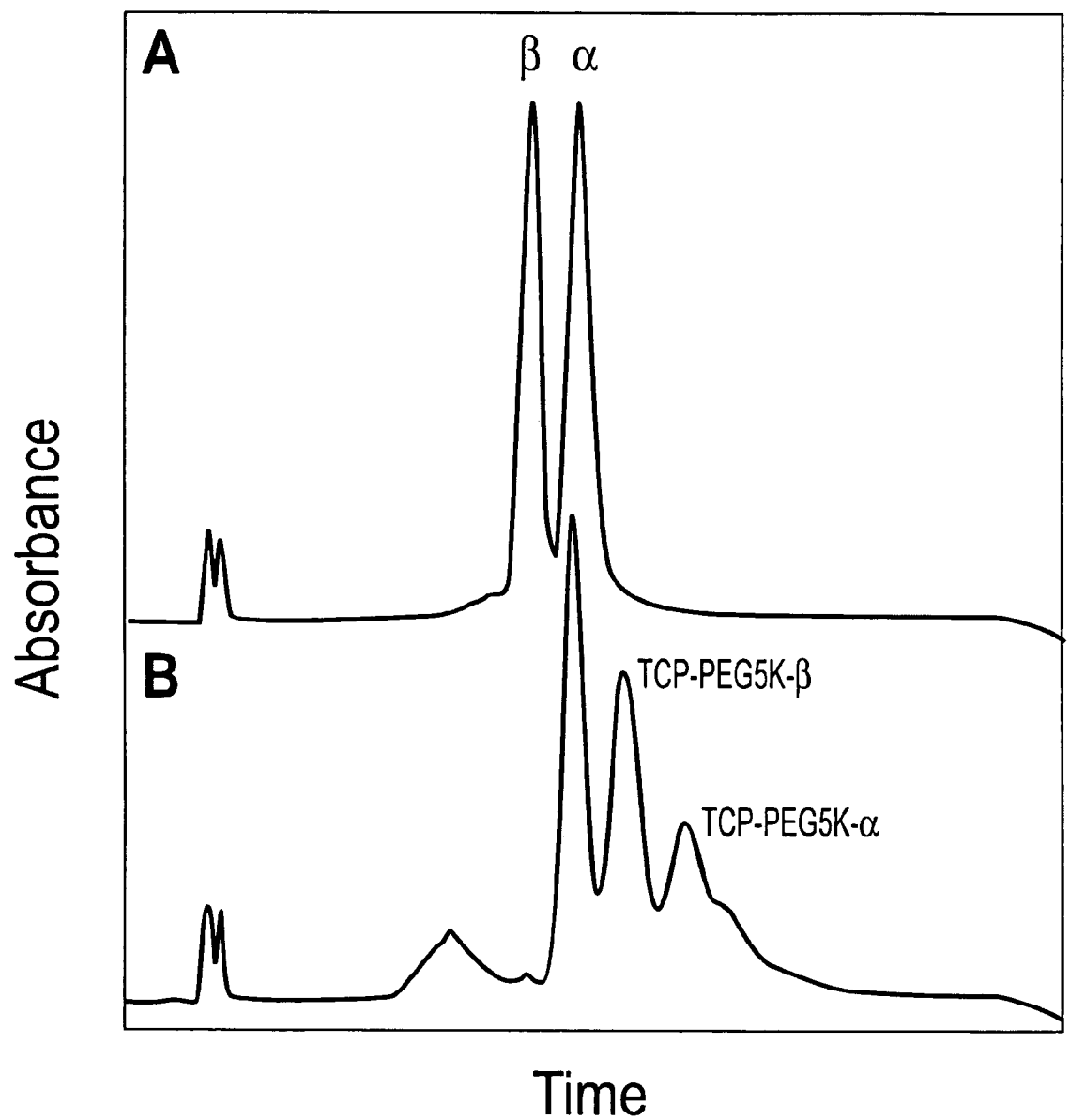
FIG. 3A–3B. RPHPLC of Hb (0.5 mM) reacted in PBS with isothiocyanato phenyl carbamate of PEG-5000 (10 mM) for 90 minutes. A: The globin chains of HbA (Trace A) are resolved into two peaks, β-globin and α-globin in the order of the elution. B: Hb reacted with isothiocyanate (Trace B) does not have any unmodified β-chain and carries four components; the unmodified α-chain and the three species of PEGylated chains. The globin chains were separated on a Vydac semi-preparative C4 column using a linear gradient of 35 to 50% acetonitrile containing 0.1% TFA. The effluent was monitored continuously at 210 nm.

Reactivity of the amino groups of HbA towards ITP-carbamoyl-PEG5K with HbA: The RPHPC map of HbA (0.5 mM) incubated with ITP-PEG5K (10 mM) at pH 7.4 and room temperature is shown in FIG. 3. Trace A shows the pattern of HbA; the elution positions of the $\alpha$ and $\beta$-globin are marked for reference. Trace B shows the RPHPLC pattern of a sample that has undergone a 90 minute reaction.

It may be seen that the β-globin is completely derivatized by the reagent in 90 minutes, but the α-globin is not modified to that level. This clearly reflects the differential reactivity of the α- and β-chains of the tetramer for PEGylation with ITP-PEG5K.

Figure 4:
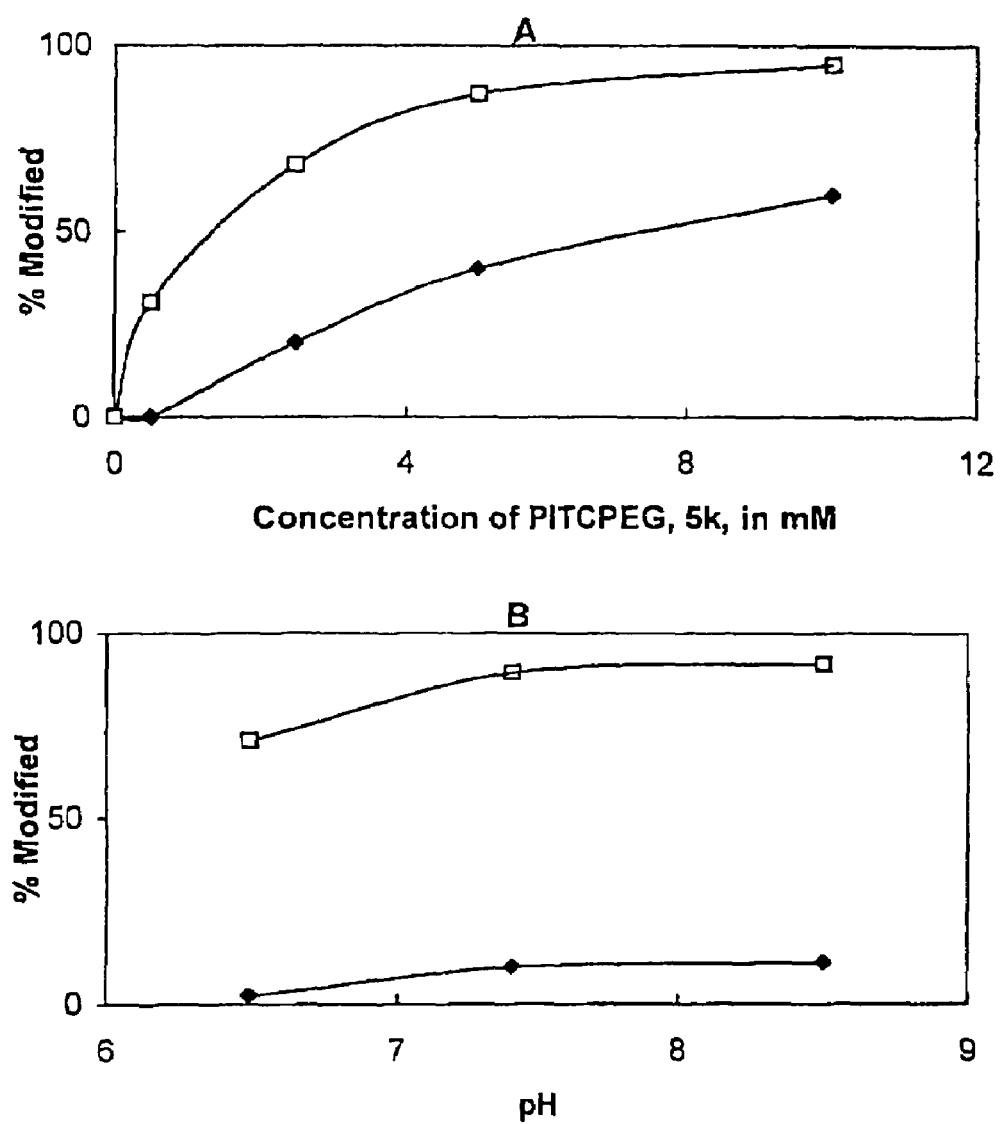
FIG. 4A–4B. Reactivity of the a and the β-chains of Hb towards isothiocyanato phenyl carbamate PEG 5000 (ITP-PEG5K) as a function of the reagent concentration. The reaction of the two chains of Hb was quantitated by the disappearance of the chains after the reaction of Hb. Panel A presents the data of the reaction of Hb (0.5 mM) with a 40 fold molar excess of the ITP-PEG5K in PBS at room temperature for 90 minutes using different concentrations of the reagent. Panel B presents the reactivity of the chains as a function of pH. The results presented are for a reaction of 180 minutes.

The differential reactivity of the two chains toward the PEG reagent is confirmed by the study of the reaction of ITP-PEG5K as a function of PEG-reagent concentration (FIG. 4). The results are shown in Panel B. Even though the β-chains is almost completely modified in the presence of 5 mM ITP-PEG5K, the α-chain is modified only to about 60% even in the presence of 10 mM ITP-PEG5K. This differential chemical reactivity of the α and of the β-chains provides the opportunity to generate molecular species site specifically modified in the β-chains.

Figure 5:
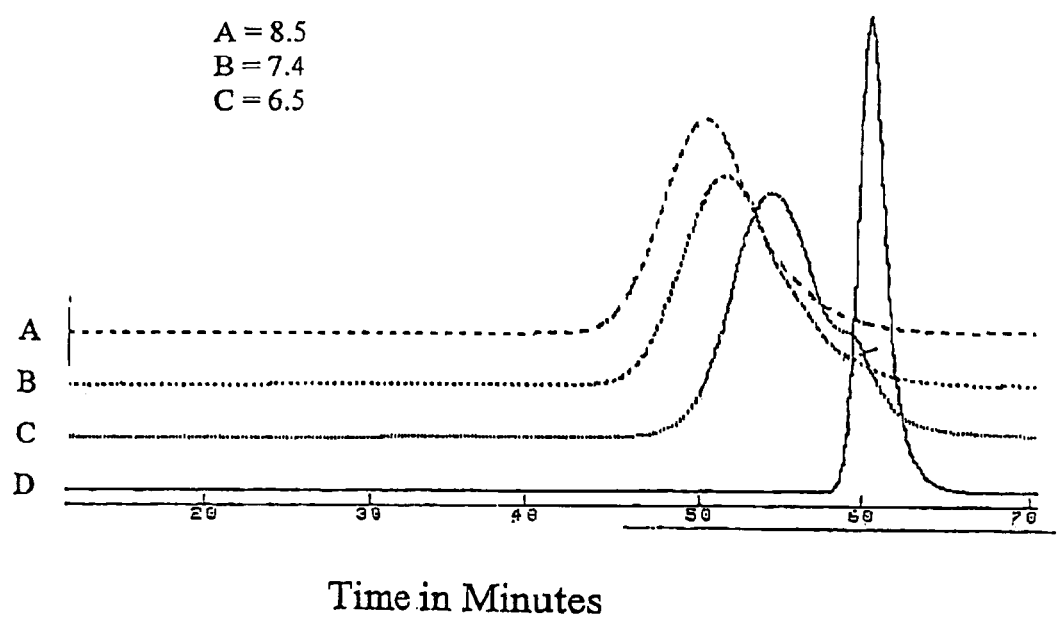
FIG. 5. Size enhancement of Hb as function of pH on reaction of Hb with ITCPEG5K. Hb (0.5 mM) was reacted in 10 mM phosphate buffer with 20 mM ITC PEG5K for 6 hours at room temperature. The size exclusion chromatography was carried out using a Pharmacia FPLC system. Two HR 10/30 Superose-12 columns connected in series were used for the size exclusion chromatography. The columns were equilibrated and eluted with PBS. The effluent was monitored at 540 nm.

PEGylation mediated size enhancement of Hb-Influence of the pH: The influence of pH on the PEGylation of Hb by ITP-PEG5K has been studied and presented in FIG. 5. The figure shows the enhancement in the molecular size of Hb as a result of PEGylation as reflected by the size exclusion chromatography. The samples of HbA (0.5 mM) were reacted with ITP-PEG5K (20 mM) for 6 hours at room temperature and then subjected to SEC on Superose 12-columns. The control HbA sample elutes at 60 minutes, and incubation with the PEG reagent enhances its apparent molecular size. The size enhancement of Hb on incubation with the PEG reagent (a 40 fold molar excess over protein) is a function of pH. When the reaction is carried at a higher pH, the size enhancement was better; the reaction at pH 8.5 gave the maximum enhancement. The peak width of the pH 8.5 reaction product was higher than that of the product generated at pH 7.5, suggesting a higher level of heterogeneity in the pH 8.5 product. The peak position of the PEG-Hb conjugated at pH 7.5 is close to that of (SP-PEG5K)$_6$-Hb suggesting that the product generated under these reaction conditions contains hexaPEGylated Hb as the major component. The generation of the hexaPEGylated Hb suggests that even though the ITP-PEG5K reagent has been designed to target primarily the PEGylation reaction to the α-amino groups, under the physiological conditions significant level of PEGylation reaction seems to be occurring at the ε-amino groups of Hb as well. Accordingly for the isolation of the ITP-PEG 5K modified Hb, the reaction in 10 mM phosphate buffer at pH 7.5 and room temperature for 6 hours has been chosen.

The reaction of HbA with ITP-PEG-5K at pH 7.4 and 4° C. for 18 hours (overnight) also generates a product that is comparable to the product generated in six hours of reaction at room temperature.

Purification of (ThioCarbamoylphenyl(TCP)-PEG5K)$_6$-Hb by ion exchange chromatography on Q-Sepharose: For the large scale purification of PEG-Hb conjugate, HbA (0.5 mM) in PBS at pH 7.4 was reacted with a forty fold molar excess of ITP-PEG 5K (20 mM) at room temperature for 7 hours. The reaction mixture was dialyzed overnight against Tris-Acetate buffer, pH 8.5 using a 13,000 to 15,000 molecular weight cut off dialysis membrane to remove the excess PEG-reagent. The dialyzed PEG-Hb conjugate was then subjected to a tangential flow filtration using Minim from PALL Corporation to get rid of the excess PEG reagent completely. A 70 K membrane was used for this filtration. The tangential flow filtration was carried out at a Hb concentration of 16 mg/ml, and filtration of the PEG reagent was followed by SEC analysis of the filtrate. The dialysis of PEG and loss of Hb during filtration has been monitored using refractive index and absorbance at 540 nm, respectively. A tangential flow filtration against about 50 volumes of the buffer yielded a product devoid of PEG reagents.

Figure 6:
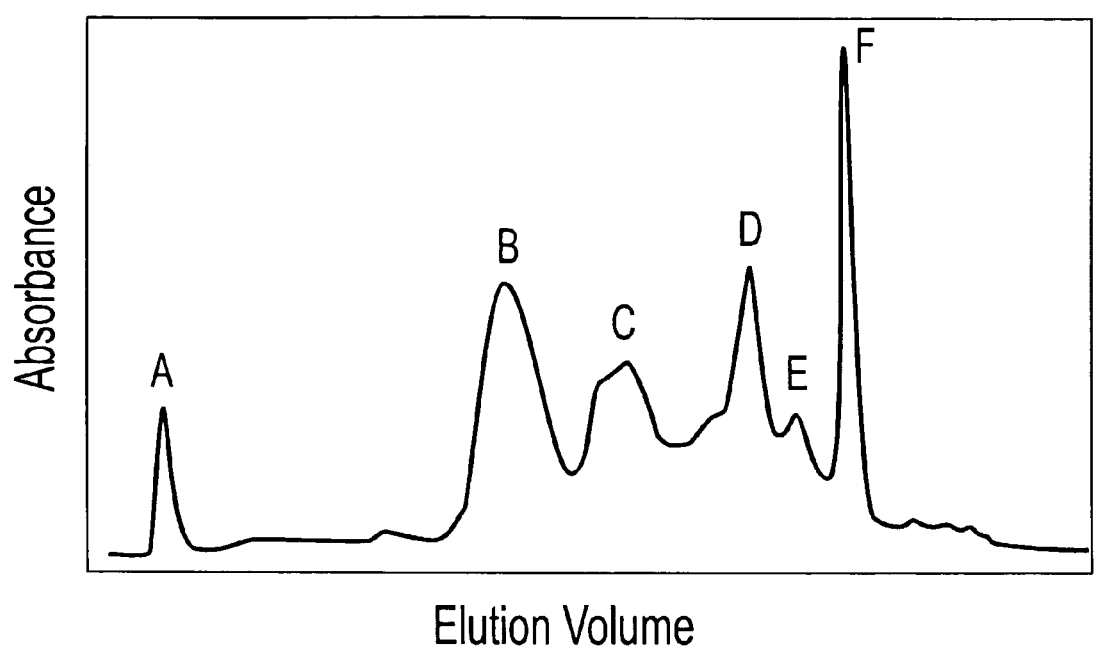
FIG. 6. Purification of (ThioCarbamoyl phenyl (TCP)-PEG5K)$_6$-Hb by ion exchange chromatogrpahy: Purification of the PEGylated products was carried out on a Q-Sepharose high performance ion exchange column (2.6×60 cm) using an Amersham Biosciences AKTA Explorer 10 Protein Purification System. The column was equilibrated with 50 mM tris-acetate buffer, pH 8.5. The protein was eluted with a decreasing pH gradient generated by the 50 mM Tris-acetate buffer pH 8.5 and 50 mM Tris-aceate buffer pH 7.0 over a eight column volume. Protein Load: 2 gms. The effluent was monitored at three wave lengths. 240, 540 and 600 nm. The protein fractions eluting from the column were named in the order of their elution, Components A to F, respectively.

The PEG-Hb conjugate present in the retentate was subjected to ion-exchange chromatographic purification on Q-Sepharose. A tris acetate buffer system of a pH gradient of pH 8.5 to 7.0 was employed to elute the PEGylated products from the column. The PEG-Hb conjugate eluted as multiple chromatographically distinct components, which are designated components A to F as indicated in the FIG. 6. Component A represents the material unadsorbed. Component B represents the major component PEG-Hb conjugate. The elution pattern of the PEG-Hb conjugate in the Figure is shown as reflected by the absorption at 540 nm (elution of Hb). A comparison of the ratio of the absorption at 540 to 240 nm (data not shown) suggests that component B is the most heavily PEGylated sample of Hb. Each of these fractions has been subjected to RPHPLC and SEC analysis. Component E has been identified as the unmodified Hb based on the RPHPLC and SEC analysis of the material. Component D appears to be predominantly Hb PEGylated on its β-chain. Component C and B carry modifications on both the a and the β-chains of Hb. The FPLC patterns of these two samples demonstrate that component C is heterogeneous as compared to B. Component B is the most prominent component of this PEG-Hb conjugate and has been isolated and used for further studies discussed below.

Figure 7:
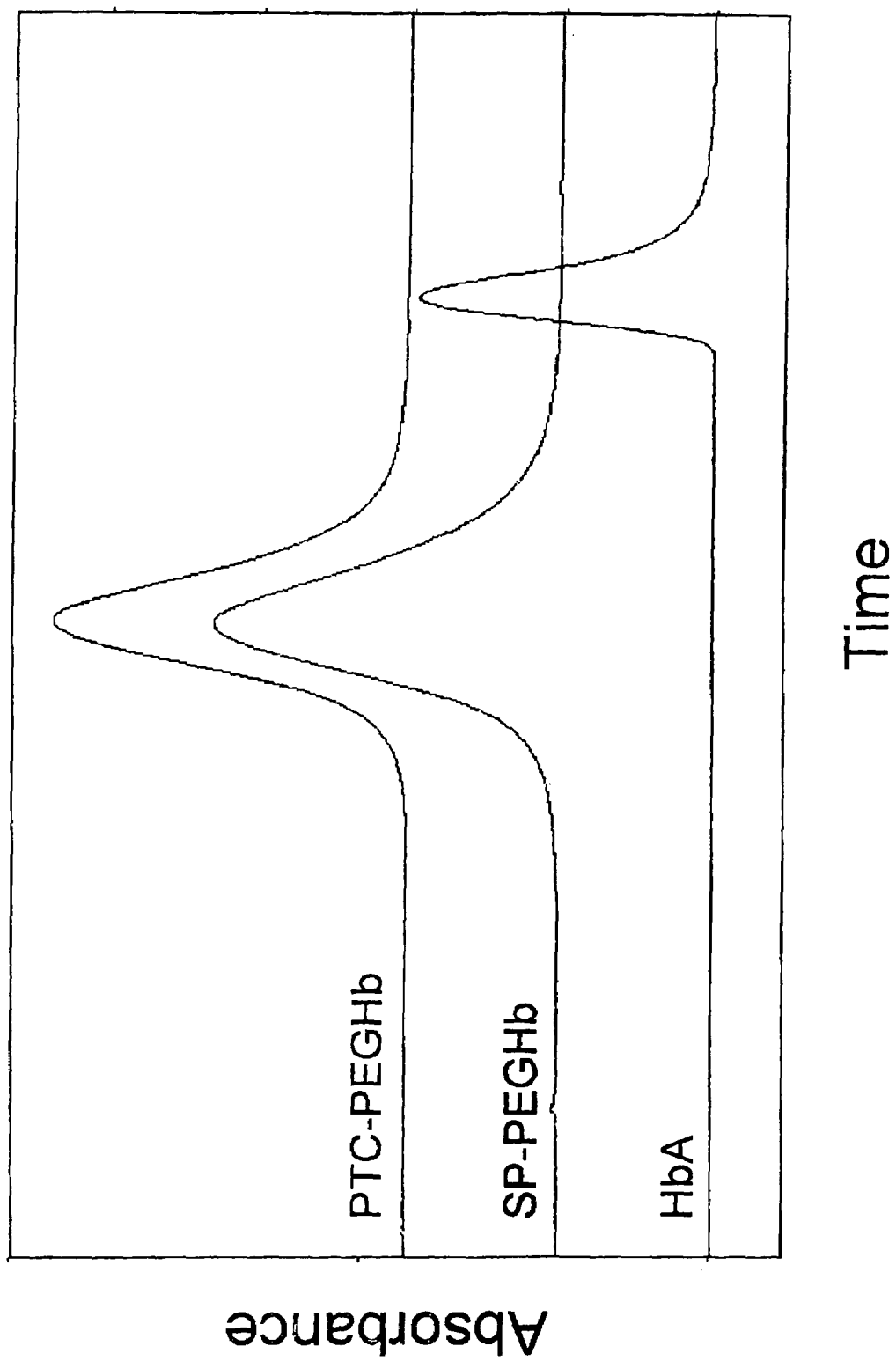
FIG. 7. Comparison of the hydrodynamic volume of component B (see FIG. 6) with that of the [(SP-PEGSK)$_6$-Hb], a hexaPEGylated Hb generated by the thiolation mediated maleimide chemistry based PEGylation of Hb. Component B of the sample of PEGylated Hb generated by isothiocyanate chemistry appears to have a hydrodynamic volume comparable to (SP-PEG5K)$_6$-Hb. Accordingly this component is referred to as (TCP-PEG5K)$_6$-Hb. SP, succinimidophenyl.

Chemical characterization of (TCP-PEG5K)$_6$-Hb (i) Size Exclusion chromatography of (TCP-PEG5K)$_6$-Hb: Component B elutes at a position corresponding to that of (SP-PEG5K)$_6$-Hb. Therefore, this new PEGylated Hb appears to be a hexaPEGylated Hb and is referred to as (TCP-PEG5K)$_6$-HbA (FIG. 7). The isoelectric focusing pattern of TCP-PEG5K Hb reflects that this material is electrophoretically homogeneous, the product showing a lower cathodic mobility relative to Hb. This is consistent with the loss of some positive charges on the surface of Hb as a consequence of the surface decoration of Hb by PEG5K chains.

Figure 8:
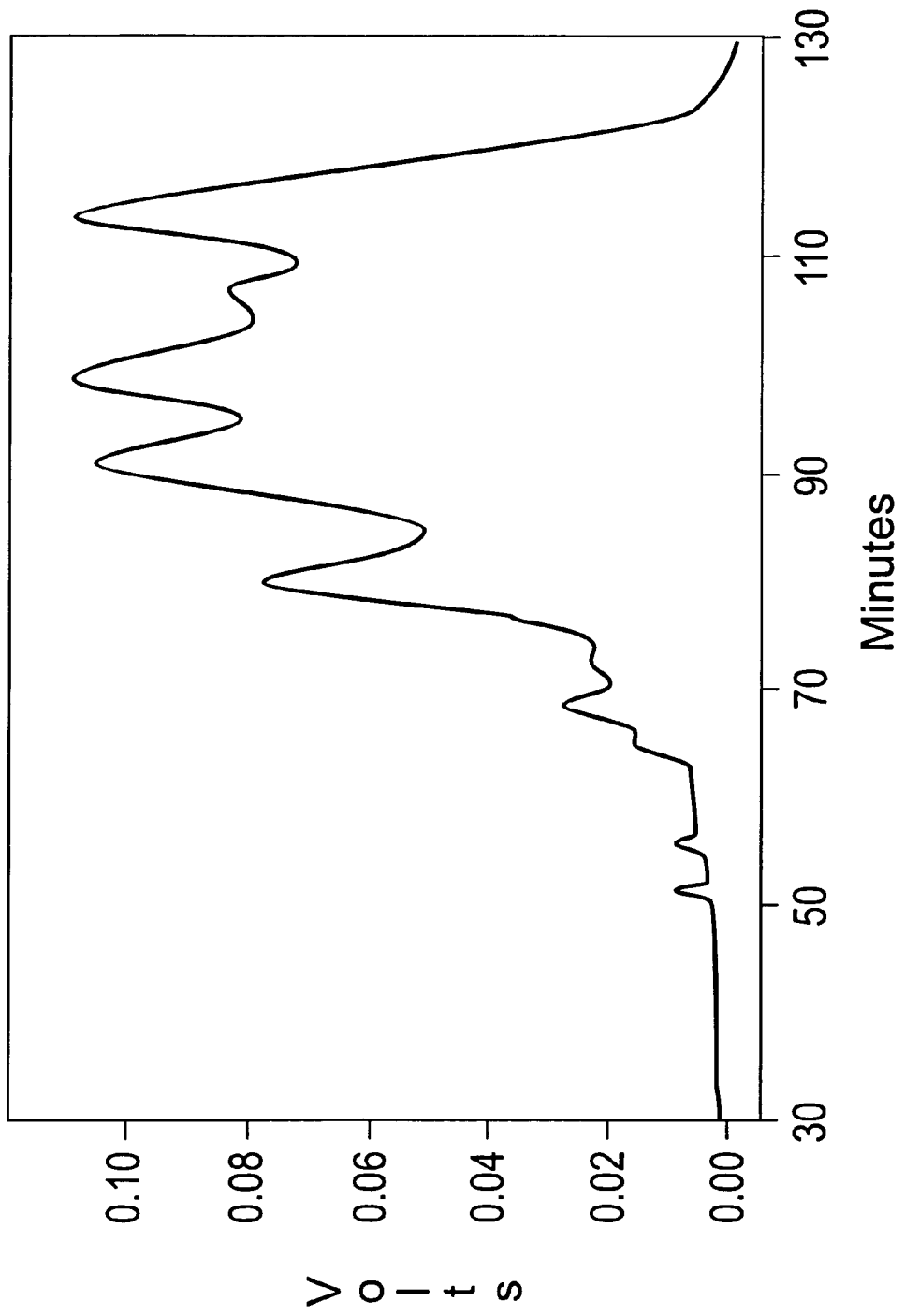
FIG. 8. RPHPLC of (TCP-PEG5K)$_6$-Hb.
Figure 9:
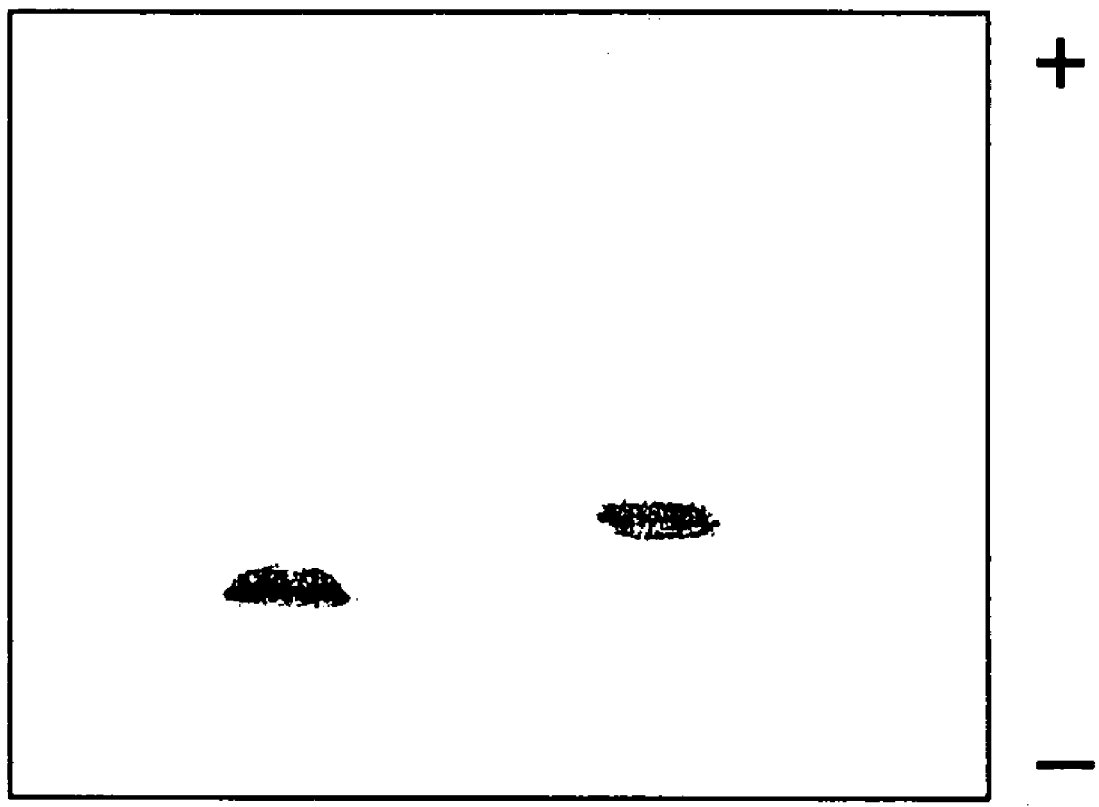
FIG. 9. Isoelectric focusing patterns of HbA and (TCP-PEG5K)$_6$-Hb.

(ii) RPHPLC map of (TCP-PEG5K)$_6$Hb: The chromatographically purified sample does not contain unmodified α- or β-chains. However, the PEG-Hb conjugate carries at least six chromatographically distinguishable globin components (FIG. 8). A homogeneous hexaPEGylated Hb is expected to contain only two globin components, one with two copies of PEG5K chains and another one with one copy of PEG5K thereby reflecting the molecular heterogeneity of the sample in terms of sites of PEGylation, even though the sample appears to be homogeneous as reflected by size exclusion chromatography or isoelectric focusing (FIG. 9).

Figure 10:
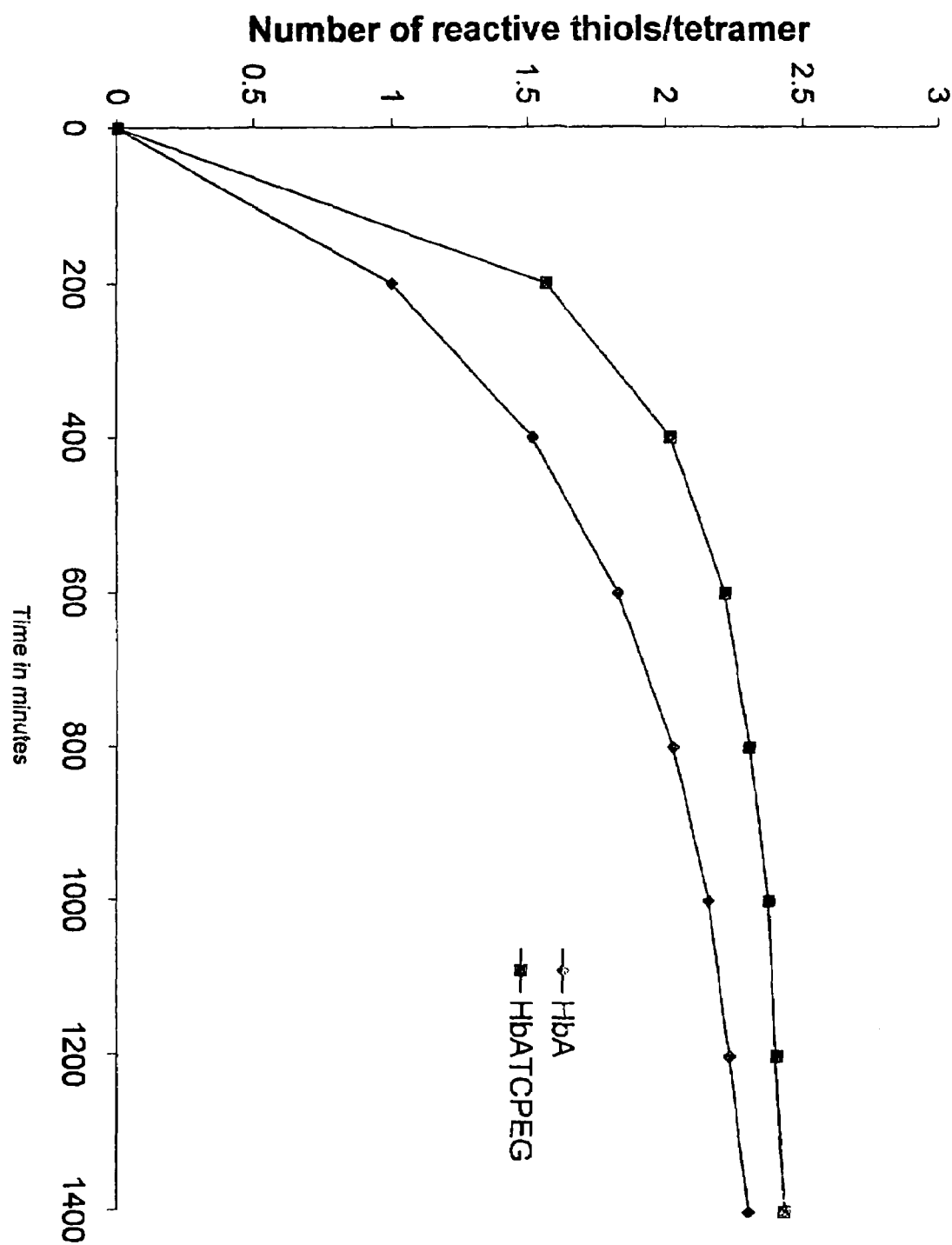
FIG. 10. Reactivity of Cys-93(β) of HbA and (TCP-PEG5K)$_6$-Hb towards 4,4'-dithiopyridine.

Chemical Characterization of (TCP-PEG5K)$_6$-Hb (i) Reactivity of thiol group of Cys-93(β): The sulfhydryl groups of cysteine (Cys) residues generally show small degree of reaction with the aliphatic isothiocyanates. The potential reaction of isothiocyanato phenyl carbamate of PEG-5000 at Cys-93(β) of (TCP-PEG5K)$_6$-Hb has been probed using the reaction of oxy Hb with dithiopyridine. As shown in FIG. 10, the new PEG-Hb adduct in its oxy conformation has two moles of fast reacting thiol groups per tetramers just as the parent Hb. Since in the parent, this reaction is with Cys-93(β), it is concluded that the aryl isothiocyanato PEG has not reacted with the thiol groups of Cys-93(β). It may also be noted from the figure that the reactivity of accessible thiol group of Cys-93(β) of HbA has been increased by the surface decoration of Hb with PEG-chains. Thus, Cys-93(β) Hb is not a site of PEGylation on reaction of Hb with ITP-PEG-5000.

Figure 11:
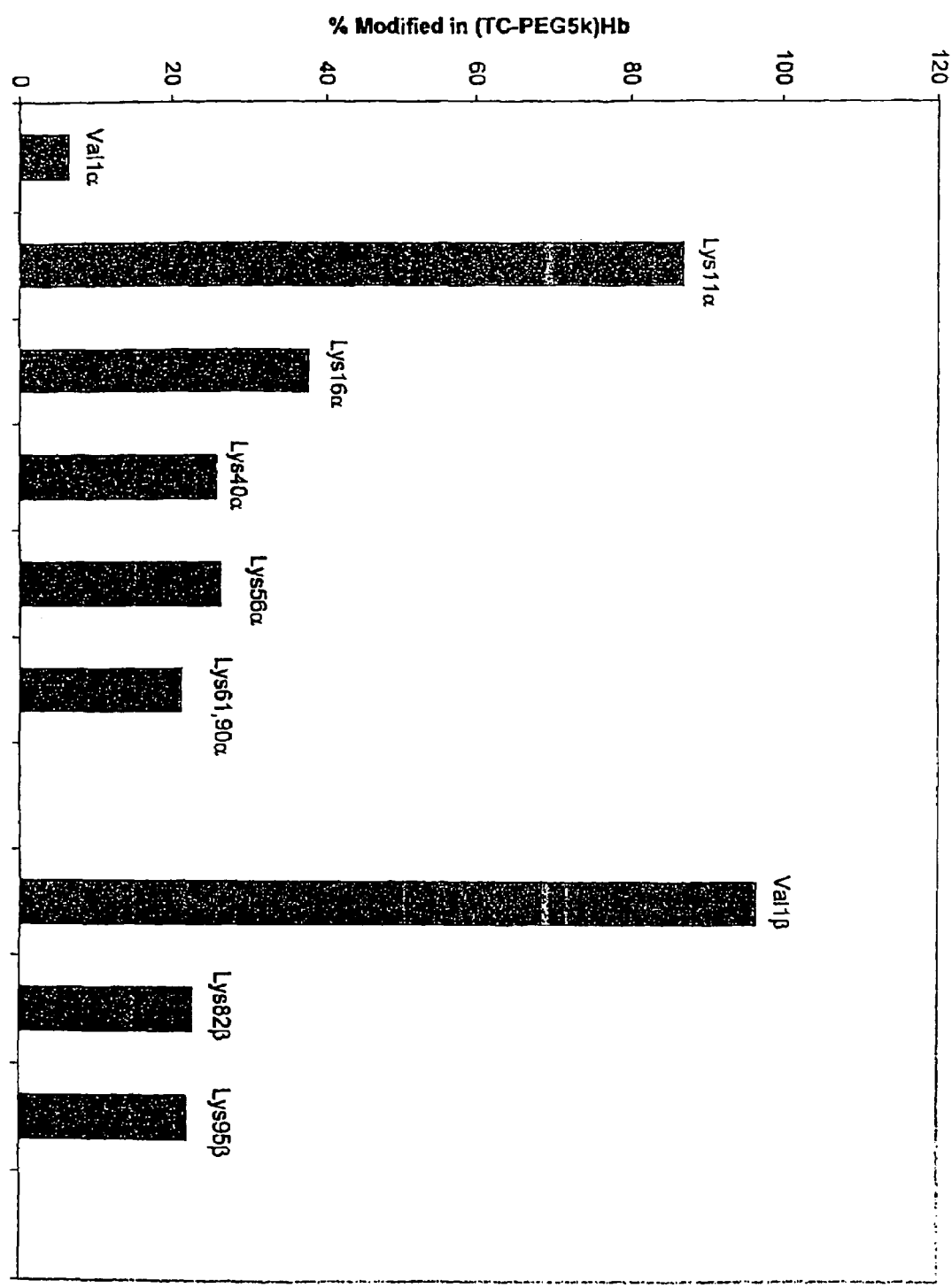
FIG. 11. Site selectivity of the conjugation of PEG5K chains by the thiocyanato chemistry.

(ii) Identification the amino groups of HbA PEGylated in (TCP-PEG5K)$_6$-Hb: The sites where the PEG couples can be found by proteolysis using trypsin, which cleaves the peptide bonds at the carboxyl side of lysine and arginine residues of the globin chains. The total globin generated by the acid acetone precipitation of HbA and (TCP-PEG5K)$_6$-Hb has been used for the tryptic peptide mapping. The results of the analysis of tryptic peptide mapping are shown in FIG. 11. The area of individual tryptic peptides in the maps has been integrated. The amount of βT$_4$, which correspond to the amino acid residues 30 to 40, that is generated by the tryptic digestion at Arg-31 and at Arg-40, has been used as a standard to compare the two maps. Since the PEGylation by the isothiocyanate chemistry is expected to be predominantly on the α-amino groups and the fast reacting ε-amino groups of Lys residues, the amount of βT$_4$ generated on tryptic digestion of the globin chains will not be influenced by the tryptic digestion. The amount of the peptides was integrated as relative to that of βT$_4$. This has permitted the calculation of the extent of PEGylation at various amino groups of Hb. The tryptic peptide βT$_1$ is completely absent in the tryptic peptide map of (TCP-PEG5K)$_6$-Hb. This peptide, which corresponds to the amino acid residues 1 to 8 of the β-chain, is absent in the tryptic peptide map. Since the amount of peptide βT$_2$, corresponding to residues 9 to 17 of the β-chains, Lys-8 is not protected from tryptic digestion, i.e. the disappearance of βT$_1$ in the map is apparently a consequence of the PEGylation of the α-amino group of Val-1(β) of βT$_1$. Based on similar analysis, the sites of PEGylation in Hb have been assigned and presented in FIG. 10. Surprisingly, the results show that the tryptic peptide αT$_1$ is not modified heavily on PEGylation, ie. the α-amino group of α-chain is not a major site of PEGylation. The results show that the ε-amino group of Lys-11 of the alpha chain is almost quantitatively modified by PEGylation. Besides these two major sites of PEGylation, the PEGylation of the Lys-16(α), Lys-40(α), Lys-56 (α), Lys-61(α), Lys-82(β) and Lys-95(β) seems to have occurred to a level of 15 to 25% in the new heaxaPEGylated Hb.

The amount of the tryptic peptide βT$_{10}$ in the PEGylated sample is in the 70% range. This peptide corresponds to the amino acid sequence 83 to 95 of the β-chain. The PEGylation of either Lys-82(β) or Cys-93(β) (which blocks the tryptic digestion at Lys-95(β)) can lower the yield of the tryptic peptide βT$_{10}$. The relatively high yield of βT$_{10}$ is consistent with that conclusion that Cys-93(β) is not PEGylated by ITP-PEG5K based on the sulfhydryl titration.

Oxygen affinity of Hb: The new PEG-Hb conjugate exhibited a high oxygen affinity in PBS buffer at 37° C. The P$_{50}$ for HbA is 14 with an n value of 2.4. The surface decoration of Hb with six copies of PEG-5K using the isothiocyanate chemistry increased the oxygen affinity, the P$_{50}$ value of the product is around 7.0 with a cooperativity around 1.7. Thus the oxygen affinity of this hexaPEGylated Hb is higher than the one generated by thiolation mediated maleimide chemistry based PEGylation. Similarly the cooperativity of this product is also lower than that of the earlier product.

Colligative properties of (TCP-PEG5K)$_6$-Hb: Based on the tryptic peptide mapping of (TCP-PEG)-Hb conjugate, along with its hydrodynamic volume being comparable to that of (SP-PEG5K)$_6$-Hb, it is concluded that this has an average of six PEG5K-chains per tetramer. Thus, the calculated molecular mass of (TCP-PEG5K)$_6$-Hb is around 95 K (Table 1), but its hydrodynamic volume corresponds to that of a globular protein with a molecular weight in the range of 250,000 daltons.

The molecular radius of (TCP-PEG5K)$_6$-Hb is around 5.8 nm whereas that of (SP-PEG5K)$_6$-Hb is around 6.8. The difference in the molecular radius of the two PEG5K-Hb conjugates on the basis molecular radius, but lack of the difference in the hydrodynamic volume as reflected in the size exclusion chromatography, is suggestive of the differential influence of the flow dynamics on the two PEG5K-Hb conjugates. Therefore, a structural role can be invoked for the activation arm, 4-mercarpto butyrimidine chain, of (SP-PEG5K)$_6$-Hb in enhancing its molecular radius relative to that of (TC-PEG5K)$_6$-Hb.

Also shown in Table 2 are data for (TCP-PEG5K)6-Hb and (TCP-DiPEG5K)$_4$-Hb comparable to the data in Table 1.

Figure 12:
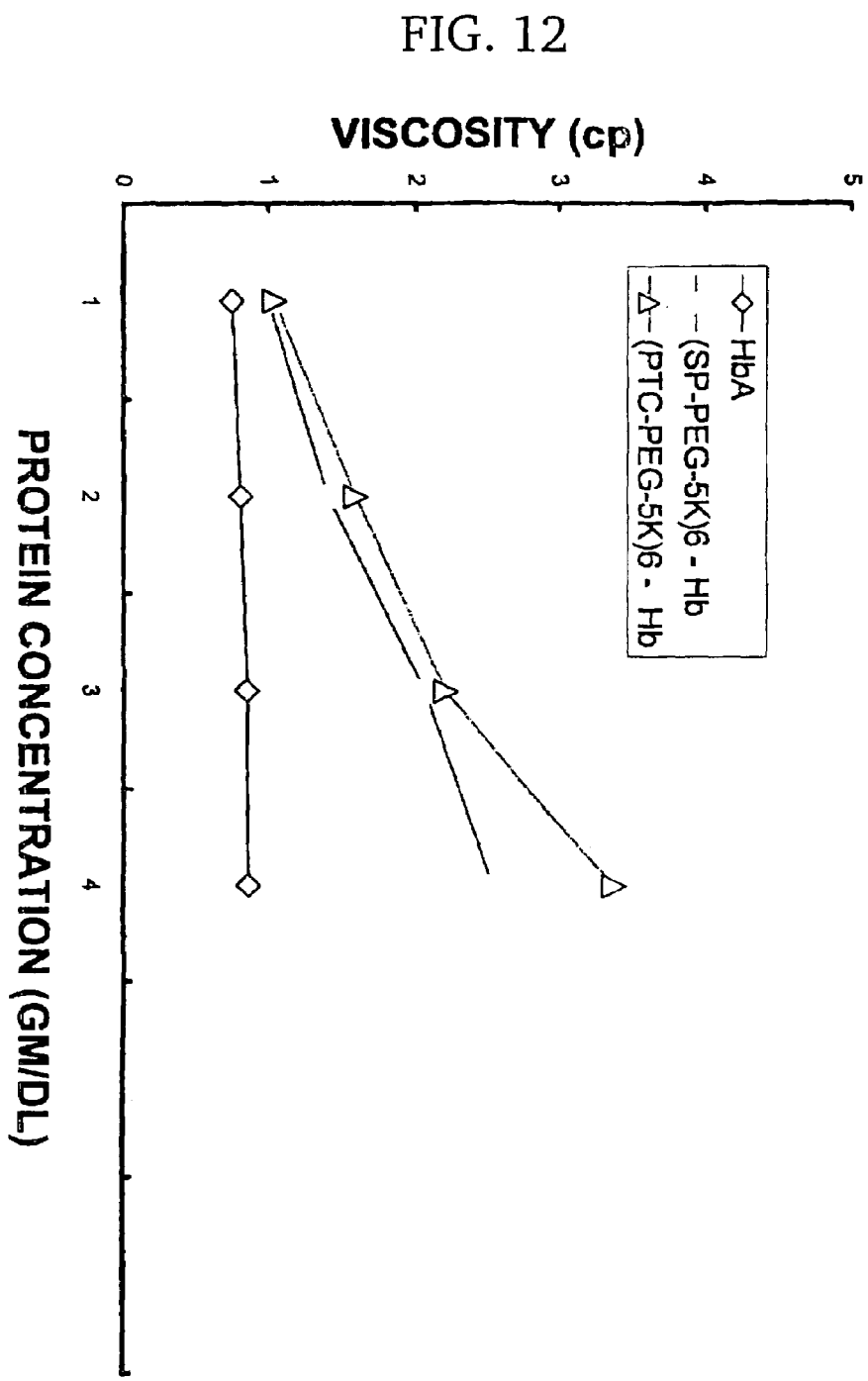
FIG. 12. Viscosity of (TCP-PEG5K)$_6$-Hb as a function of protein concentration.

The results presented in FIG. 12 depict the viscosity of (TCP-PEG5K)$_6$-Hb as a function of protein concentration and compared with that of control HbA. The results demonstrate that the surface decoration of Hb increases the viscosity of HbA. The viscosity of this new material also appears to be slightly higher than that of (SP-PEG5K)$_6$-Hb.

Figure 13:
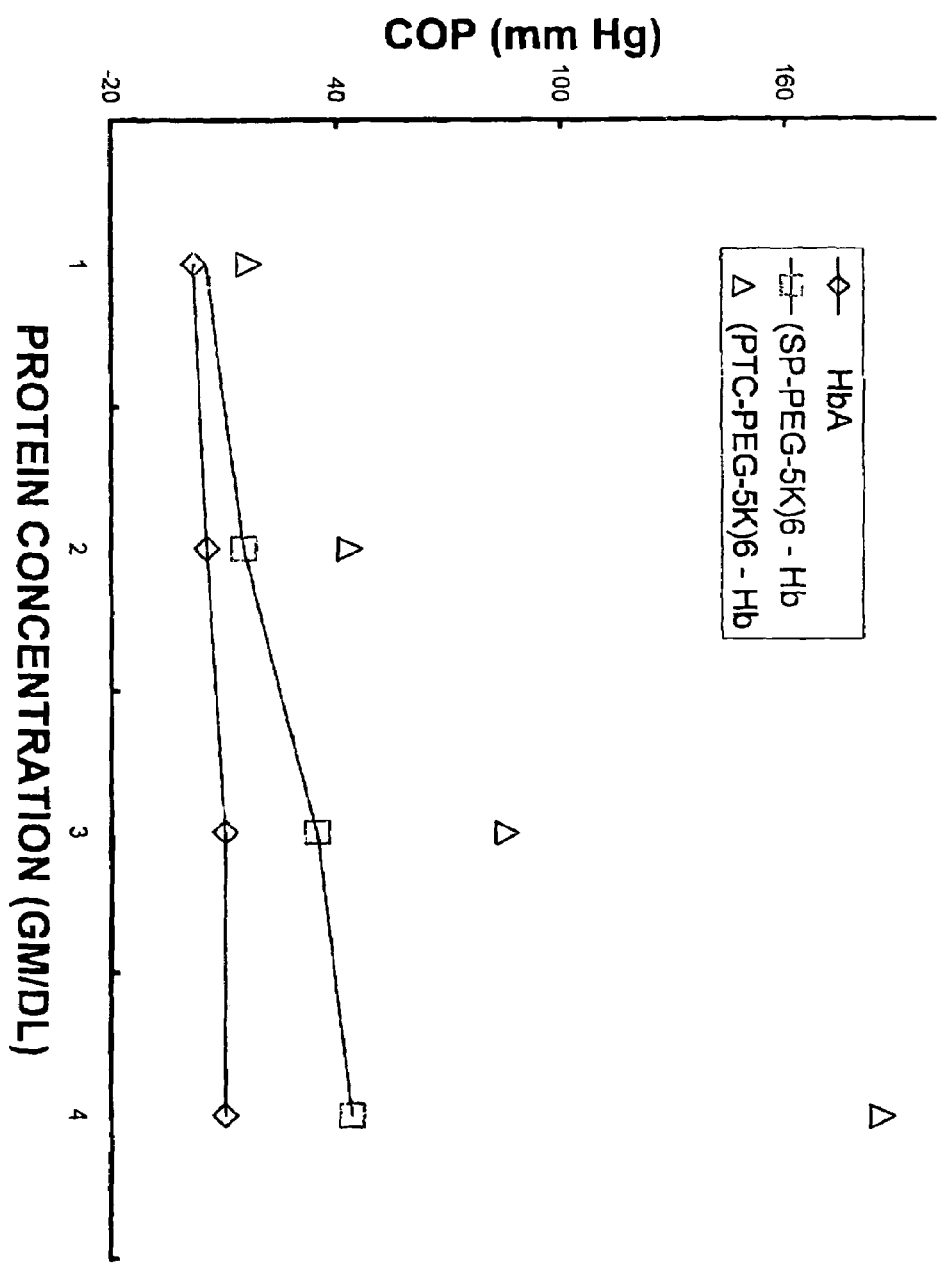
FIG. 13. Colloidal oncotic pressure of (TCP-PEG5K)$_6$-Hb as a function of protein concentration.

The colloidal oncotic pressure of (TCP-PEG5K)$_6$-Hb is presented in FIG. 13 as a function of protein concentration and compared with that of Hb. As anticipated, PEGylation of Hb increased the colloidal oncotic pressure. Though (TCP-PEG5K)$_6$-Hb is also a hexaPEGylated Hb, the increase in the colloidal oncotic pressure of Hb at a given protein concentration is remarkably higher than that of the hexaPEGylated Hb, (SP-PEG5K)$_6$-Hb generated earlier by the thiolation mediated PEGylation protocol.

Figure 14:
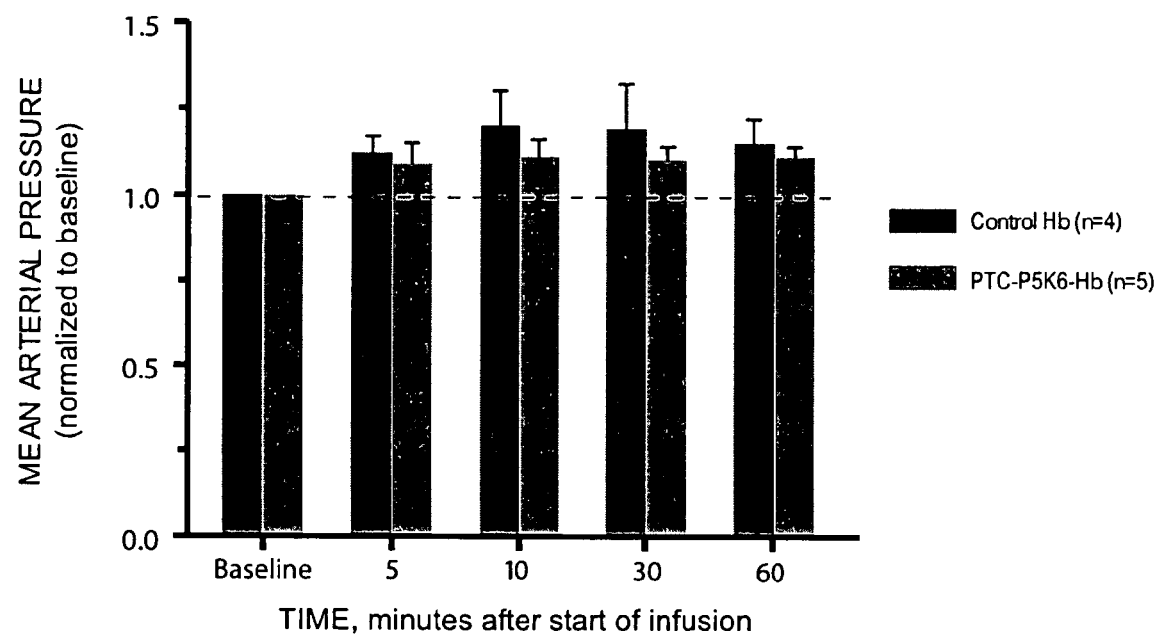
FIG. 14. Mean arterial pressure and heart rate of hamsters after 10% top load with (TCP-PEG5K)$_6$-Hb.
Figure 14:
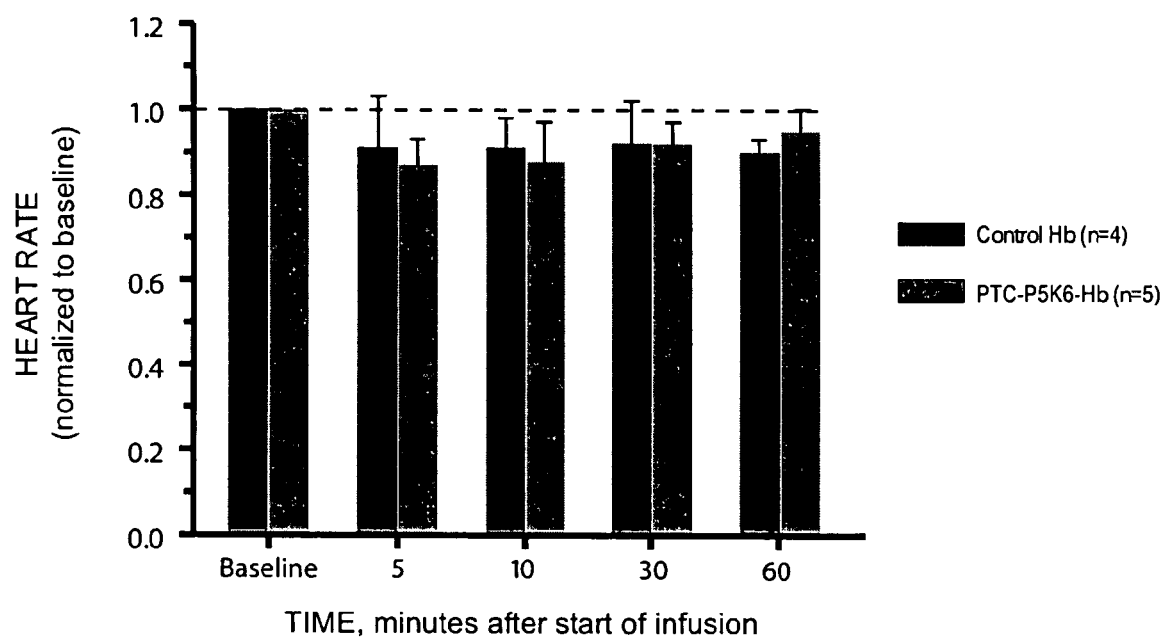
Figure 15:
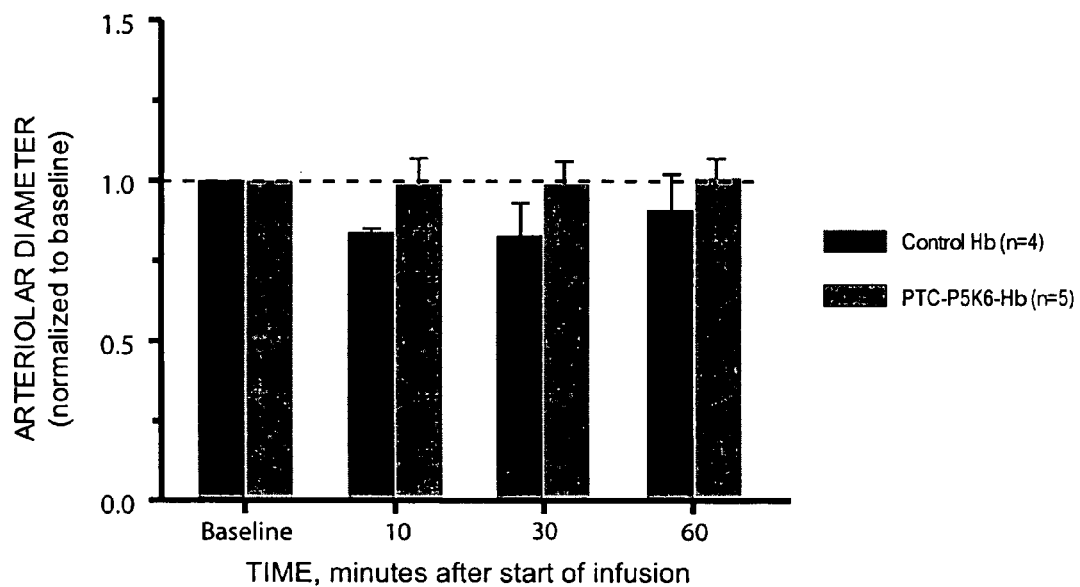
FIG. 15. Influence of 10% top load of hamsters with (TCP-PEG5K)$_6$-Hb on the arteriolar and venular diameter.
Figure 15:
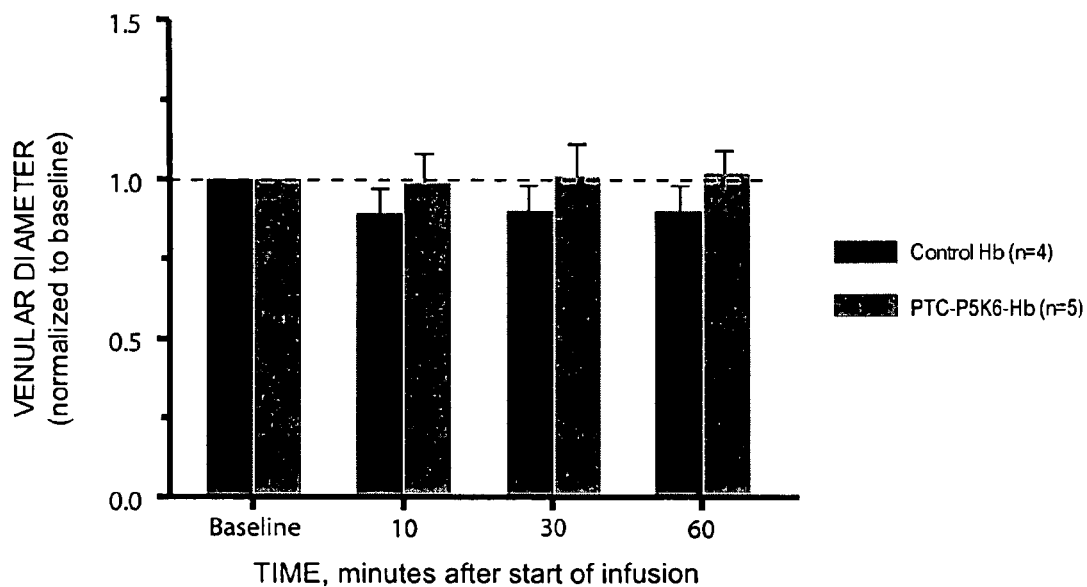
Figure 16:
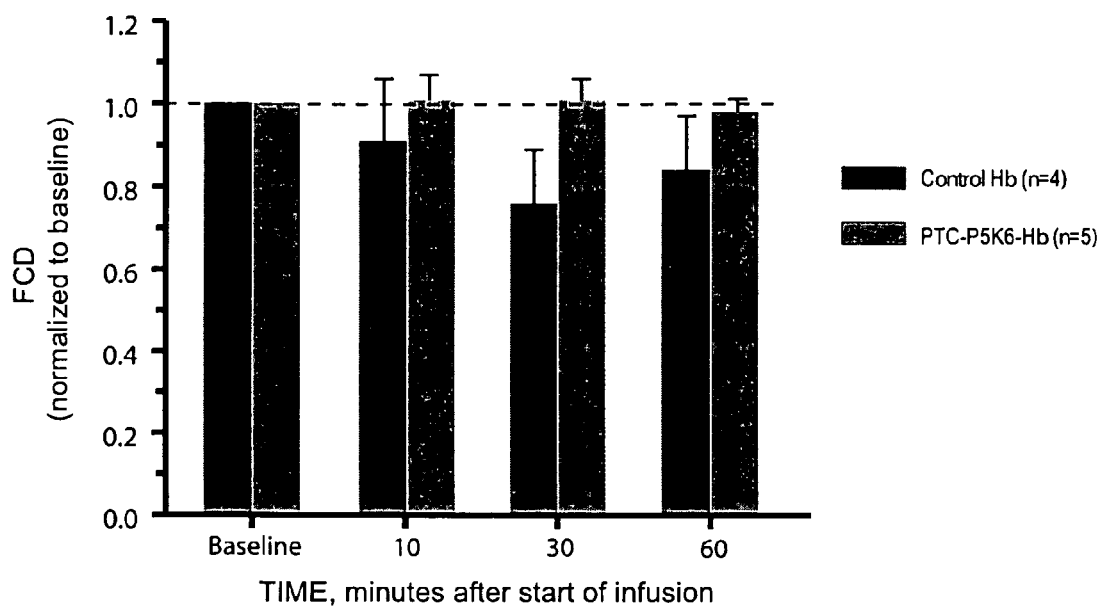
FIG. 16. Influence of 10% top load of hamsters with (TCP-PEG5K)$_6$-Hb on the functional capillary density and vascular resistance.
Figure 16:
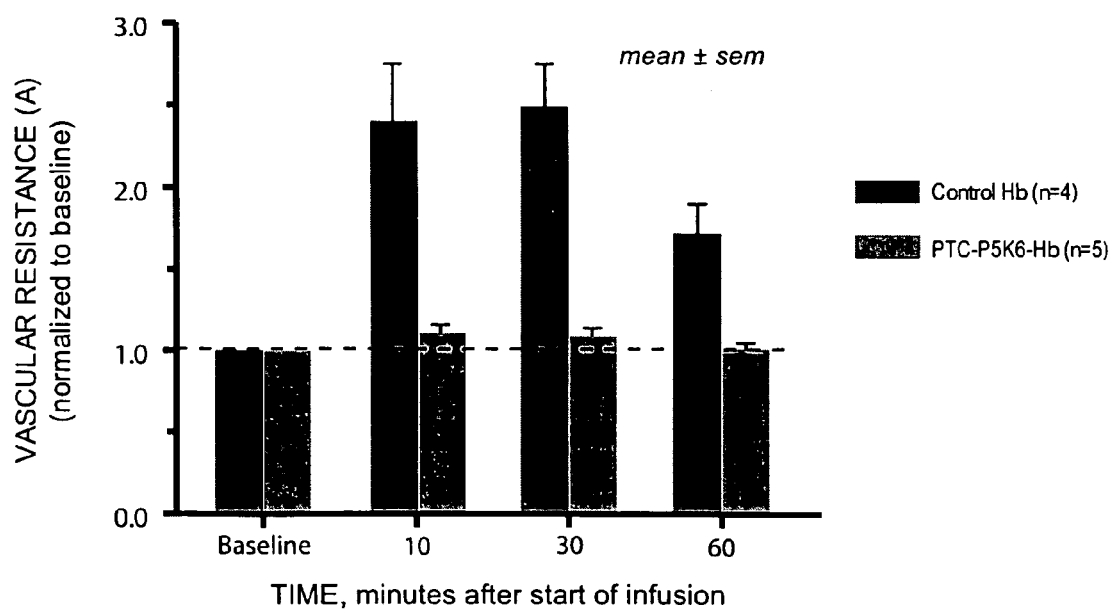

Vasoactivity of (TCP-PEG5K)$_6$-Hb in 10% top load Awake Hamster Window Model: Comparison of the systemic and micro-vascular response to (TCP-PEG5K)$_6$-Hb: The changes in the mean arterial pressure resulting from infusion of (TCP-PEG5K)$_6$-Hb into the hamster has been compared with that of a control Hb sample as a function of time. The new PEG-Hb did show some increase in the pressure as compared to its base value, and remained nearly the same throughout the sixty minute period of the observation. The increase in blood pressure with the control sample is slightly higher than that with the new PEG-Hb conjugate. Even after sixty minutes, the pressure remains slightly higher than that of PEG-Hb conjugate. Both the control and PEGylated Hb resulted in a slight reduction in the heart rate as a result of infusion. Though, the conjugation of PEG onto Hb appeared to have small but noticeable attenuation of the effect on changes in the heart rate, the difference is small (FIG. 14). At the microvascular level, the arteriole and the venular diameter did not change significantly on infusion with the new PEG-Hb conjugate as compared to its baseline values. On the other hand, the animals infused with unPEGylated Hb (control Hb) showed some reduction in their arteerolar and venular tone as compared to the pre-infusion values (FIG. 15). The functional capillary density that represents the number of the perfused capillaries also remains the same as the base line, for the sixty minutes of the observation period. In contrast, the functional capillary densities in animals infused with control Hb were lower as compared to the pre-infusion values. The vascular resistance in the animals infused with PEG-Hb conjugate is same as the baseline values, while the animals infused with unmodified Hb exhibited a significant increase in the vascular resistance that remained high during the period of observation (FIG. 16). The results clearly establish that the surface decoration of Hb with six copies of PEG 5K-chains using isothiocyanate chemistry neutralizes the vasoactivity of the control Hb sample.

TABLE 1

Comparison of the Solution Properties of HexaPEGylated Hbs

|  | (SP-PEG5K)$_6$-Hb | (TC-PEG5K)$_6$-HbA |
| --- | --- | --- |
| Molecular Mass (K) | 95 K | 95 K |
| Molecular Radius (nm) | 6.8 | 5.8 |
| Viscocity* (cPs) | 2.8 | 3.33 |
| Oncotic Pressure (mmHg) | 65 | >200 |

*These measurements were made at a Hb concentration of 4 gms/dL at room temperature in phosphate buffered saline, pH 7.4.

TABLE 2

Comparison of the Solution Properties of PEGylated Hbs

|  | (TCP-PEG5K)6-Hb | (TCP-DiPEG5K)$_4$-HbA |
| --- | --- | --- |
| Molecular Mass (K) | 95 K | 105 K |
| Molecular Radius (nm) | 5.8 | 6.5 |
| Viscocity* (cPs) | 3.3 | 6.5 |
| Oncotic Pressure (mm Hg) | >200 | >200 |

*These measurements were made at a Hb concentration of 4 gms/dL at room temperature in phosphate buffered saline, pH 7.4.

PEGylation of Hemoglobin Using Acylation Chemistry

Figure 19:
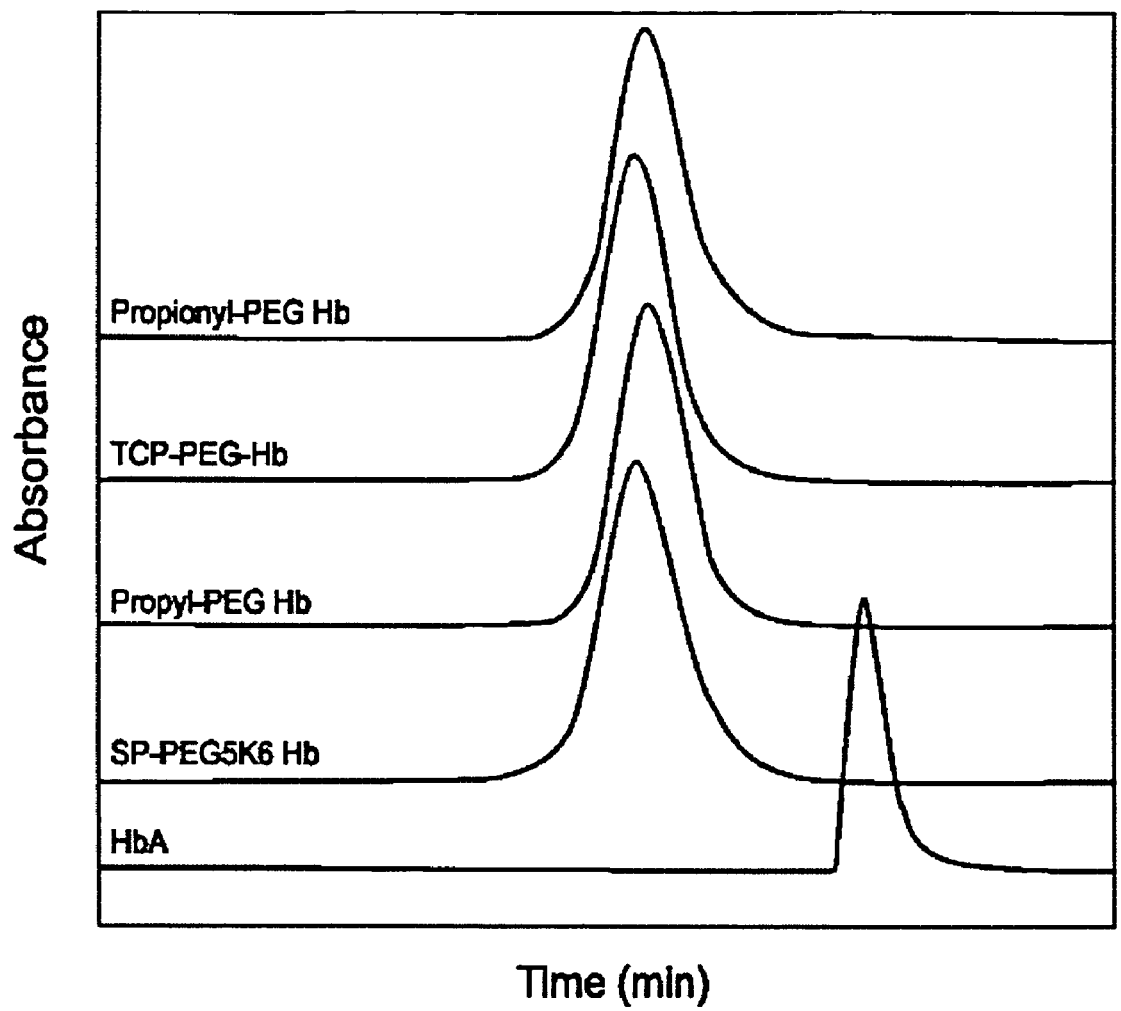
FIG. 19. Size exclusion chromatographic profiles of PEGylated Hbs generated by different chemical approaches: Thiolation mediated maleimide chemistry based PEGylation, (SP-PEG5K)$_6$-Hb; reductive alkylation chemistry, (Propyl PEG-Hb); thiocarbamoylation chemistry (TCP-PEG-Hb); and acylation chemistry (Propionyl PEG-Hb).

PEGylation of hemoglobin using either the above-described isothiocyanato phenyl PEG or using acylation chemistry results in an alteration of the surface charge of hemoglobin (non-conservative PEGylation), in contrast to the conservative PEGylation produced using thiolation mediated maleimide chemistry (19) or using PEG aliphatic aldehyde (46). In non-conservative PEGylation, the PEGylation of the amino groups of Hb is accompanied by neutralization of the positive charge at the site of covalent attachment of the PEG-chain. The structure of the conjugating group in each of the PEGylated Hbs generated using the four above indicated PEGylation chemistries is schematically presented in FIG. 18A–18D. The new conjugation chemistries described herein have been optimized to produce PEGylated Hbs that are isohydrodynamic volume with the non-hypertensive hexaPEGylated Hb generated by the thiolation mediated maleimide chemistry based PEGylation. The size exclusion chromatographic profiles of the PEGylated Hbs produced by the four different chemistries using PEG5K functionalized with the appropriate group specific reagents are compared FIG. 19. The hydrodynamic volume of (SP-PEG5K)$_6$-Hb corresponds to that of intermolecularly cross linked Hb with a molecular mass of 256,000 daltons (four Hb tetramers intermolecularly cross linked using maleimidophenyl PEG-600 (24). Analysis of the SDS-PAGE pattern and the tryptic peptide mapping of the four PEGylated Hbs has suggested that these PEGylated Hbs carry, on an average six copies of PEG-5K chains per Hb molecule. These results suggest that the enhancement in the hydrodynamic volume of Hb resulting as a consequence of conjugation of PEG-chains is a direct correlate of the PEG mass conjugated to Hb. Similar results were observed earlier with site specifically PEGylated Hbs wherein different PEG masses were conjugated at the two Cys-93(β) residues of Hb by maleimide chemistry. These results also indicated that a given mass of PEG increases the hydrodynamic volume of the Hb six to eight times higher than that by a globular protein of similar molecular mass. The data presented in FIG. 19 suggest that the chemistry of conjugation does not influence this correlation between the apparent increase in the molecular volume of Hb and PEG-mass.

Site Selectivity of PEGylation in the Isohydrodynamic Volume PEGylated Hbs: Although the four PEGylated Hbs exhibit molecular size homogeneity (i.e. in terms of hydrodynamic volume), they are not biochemically homogeneous species. However, the PEGylation reaction is not random and is limited to a few surface amino groups of Hb. For example, in (SP-PEG5K)$_6$-Hb, the product generated by the thiolation mediated maleimide chemistry based PEGylation, Cys-93(β) is modified quantitatively. The sites of PEGylation in (SP-PEG5K)$_6$-Hb are Cys-93(β), Lys-60(α), Lys-120 (β), Lys-11(α), Lys-8(β), Val-1and Val-1(β), in decreasing order of reactivity. In the other three PEGylated Hbs, the —SH group of Cys-93(β) is not derivatized. In the PEGylated Hb generated by thiocarbamoylation [thiocarbamoyl phenyl PEG-Hb, (TCP-PEG-Hb)], four of the six PEG 5K-chains are on the α-amino groups of the two Val-1(β) and the ε-amino groups of two Lys-11(α) of the tetramer. The other two PEG-chains are distributed on a limited number of surface ε-amino groups. The site selectivity in the PEGylated Hb derived through reductive alkylation chemistry, (Propyl PEG-Hb), overlaps with that achieved through the thiocarbamoylation chemistry. In contrast, the site selectivity in the PEGylated Hb derived through the acylation (active-ester) chemistry, Propionyl-PEG Hb, exhibits a partial overlap with that observed with the reductive alkylation and the thiocarbamoylation chemistries. The major sites of PEGylation in this case are Val-1(α), Val-1(β) and Lys-11 (α). The PEGylation of Val-1(β) and Lys-11(α) is a common feature among the new chemistries described herein. The pattern of PEGylation achieved through thiolation mediated maleimide chemistry based PEGylation is very distinct from that achieved through the other three PEGylation protocols. However, the number of PEG5K chains conjugated to Hb in all these cases is around six, and the differences in the site selectivity of the PEGylation appears to have little influence on the hydrodynamic volume of the PEGylated product (size enhancement). Thus, the number of PEG-chains and the molecular mass of the PEG-chains used for the surface decoration appear to dictate the hydrodynamic volume of the resulting PEGylated Hb.

Figure 20:
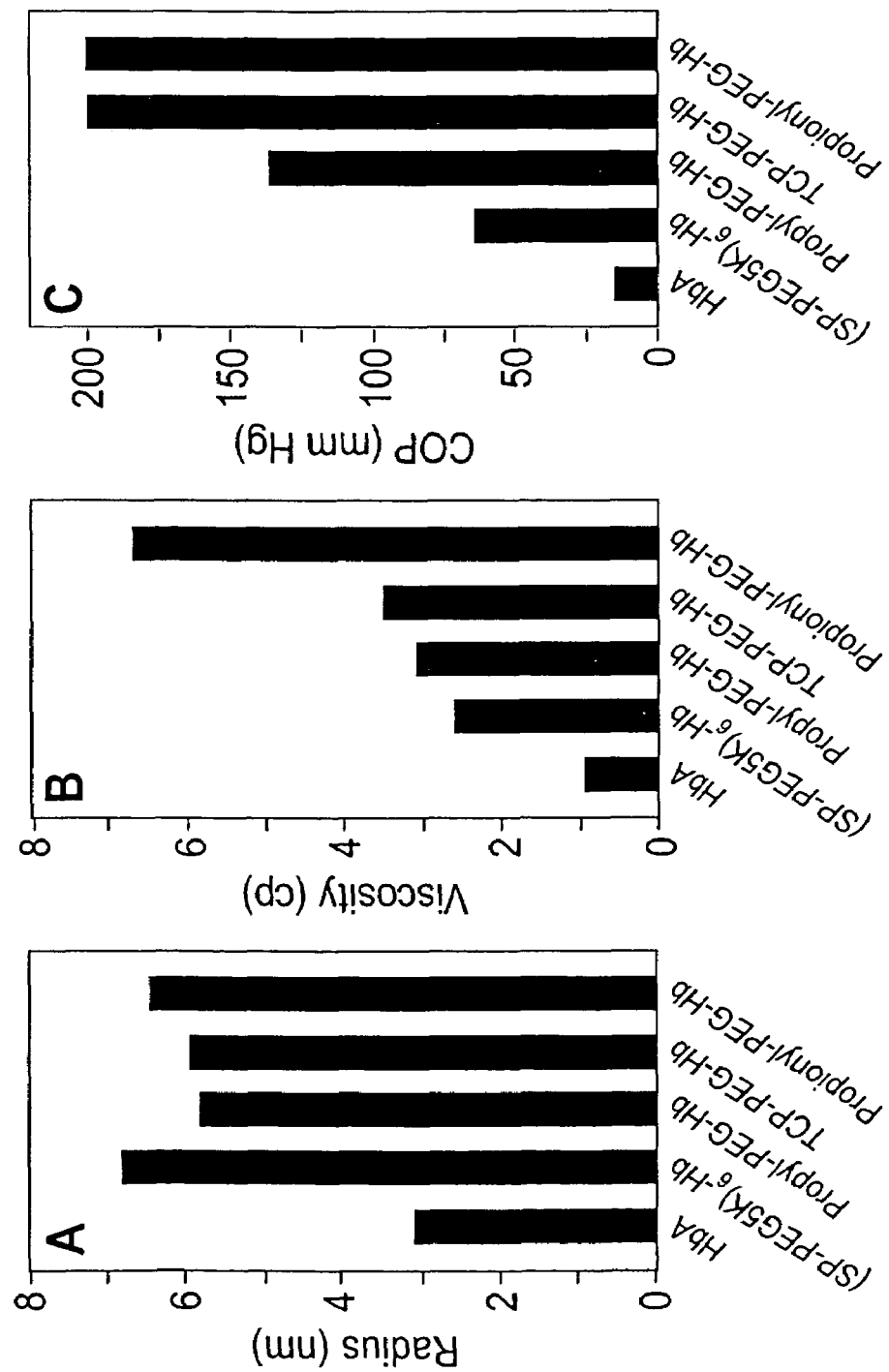
FIG. 20A–20C. Physical properties of PEGylated Hb (A) molecular radius (B) viscosity and (C) colloidal osmotic pressure. All measurements were carried out in 10 mM phosphate buffered saline, pH 7.4. The viscosity and colloidal osmotic pressure were measured at a Hb concentration of 4 g/dL.

Molecular Radius of the Isohydrodynamic Volume PEGylated Hbs: The molecular radius of the hexaPEGylated Hbs generated by the four different chemistries as determined by dynamic light scattering is presented in FIG. 20A. As can be seen, the molecular radius of Hb is nearly doubled on its surface decoration with about six copies of PEG-5K chains. Thus, the molecular volume enhancement resulting on PEGylation appears to be a direct correlate of the number of PEG5K chains on the surface of Hb, and is not significantly influenced by the chemistry of conjugation.

Relative Viscosity of Isohydrodynamic Volume PEGylated Hbs: The data on the relative viscosity of the four PEGylated Hbs is presented in FIG. 20B. The four hexaPEGylated Hbs could be classified into two groups. The viscosities of the hexaPEGylated Hbs generated by thiolation mediated maleimide chemistry, reductive alkylation chemistry and thiocarbamoylation chemistry are very close, and are nearly three to four times that of control Hb. In contrast, the viscosity of the PEGylated Hb generated by acylation chemistry is more than six times that of control Hb.

Colloidal Osmotic Pressure of Isohydrodynamic Volume PEGylated Hbs: The colloidal osmotic pressure of the four PEGylated Hbs is compared with that of the unmodified Hb in FIG. 20C. TCP-PEG-Hb and Propionyl-PEG-Hb, the two PEGylated Hbs that have lost the positive charge of the amino groups PEGylated (non-conservatively PEGylated Hbs), exhibit the highest COP. The colloidal osmotic pressure of the conservatively PEGylated Hbs, $(SP-PEG5K)_6$-Hb and Propyl PEG-Hb, is lower than that of the non-conservatively PEGylated Hbs, the colloidal osmotic pressure of $(SP-PEG5K)_6$-Hb being the lowest, and that of the Propyl-PEG-Hb being intermediate. Thus, neutralization of the positive charges of the amino groups as a consequence of PEGylation endows a higher increase in the colloidal osmotic pressure to Hb on a PEG mass basis as compared to the PEGylation that conserves the positive charge of the amino group that is PEGylated. In addition, the presence of an extension arm between the protein and the conjugating group appears to further lower the propensity of the PEGylation to increase the colloidal osmotic pressure of Hb.

IV. Discussion

As described herein, isothiocyanato phenyl carbamate of PEG5K (ITP-PEG5K) has been designed and developed as a PEGylating reagent that can target the PEGylation reaction of proteins to the α-amino groups and the reactive ε-amino groups of Lys residues under physiological conditions. Reaction of ITC-PEG5K with Hb has been optimized to isolate a hexaPEGylated $(TCP-PEG5K)_6$-Hb (TCP=ThioCarbamoyl phenyl). The hexaPEGylated Hb exhibits a hydrodynamic volume comparable to that of another non-hypertensive hexaPEGylated Hb, $(SP-PEG5K)_6$-Hb designed and generated using a thiolation mediated, maleimide chemistry based PEGylation protocol. In the $(TCP-PEG5K)_6$-Hb, the PEGylation was distributed, predominantly, on the amino groups of Val-1(β) and Lys-11(α) (100 and 90% respectively) and to a lower level at the ε-amino groups of Lys-16(α) (~38%), Lys-40(α) (~25%), Lys-56(α) (~25%), Lys-61(α) and/or Lys-90(α) (~20%), Lys-82(β) (~20%), and Lys-95(β) (20%). However, the PEGylation at Val-1(α) was negligible. The viscosity of the solution of $(TCP-PEG5K)_6$Hb is slightly higher than that of $(SP-PEG5K)_6$-Hb. On the other hand, its colloidal onctoic pressure is significantly higher than that of $(SP-PEG5K)_6$-Hb. The absence of the mercapto-butyrimidyl extension arm in $(TCP-PEG5K)_6$-Hb between Hb and the PEG-chain, and a site selectivity of PEGylation in this PEG-Hb conjugate that is distinct from that in $(SP-PEG5K)_6$-Hb, i.e., differences in the chemistry of the conjugation of PEG to Hb, may be contributing factors to this difference. The studies on the systemic and microvascular response in the hamster to a 10% top load infusion of a 4 gms % solution of $(TCP-PEG5K)_6$-Hb demonstrated that at a 0.4% plasma Hb concentration, this PEGylated Hb did not cause significant changes in mean arterial blood pressure and heart rate. At the microvascular level, the number of perfused arteries, the arteriolar and vascular tone established that PEGylation reverses the vasoactivity of Hb. The development of this non-hypertensive hexaPEGylated Hb using isothiocyanato chemistry provides new opportunities for the developing PEGylated Hbs as potential Hb based oxygen carriers.

Surface decoration of Hb with PEG5K-chains appears to modulate the vasoactivity of acellular Hb in vivo without significantly influencing its NO binding activity in vitro. A preparation of hexaPEGylated Hb generated by thiolation mediated, maleimide chemistry based conseravative PEGylation of Hb has been found to be non-hypertensive. Accordingly, the PEGylated Hb are likely to be devoid of Hb-vasoactivity mediated toxicity when these are used as potential Hb based oxygen carriers.

It has been suggested that, the modulation of the vasoactivity of Hb on PEGylation is a consequence of the PEGylation induced viscosity and colloidal onctotic pressure of Hb solution, which is a correlate of the amount of the PEG-chains (PEG-mass) conjugated to Hb. This conclusion implies that the chemistry of the conjugation of PEG-chains to Hb and the pattern of the surface decoration of Hb with the PEG chains does not play any role in the modulation of the 'pressor effect' of Hb. However, a recent study has shown that the pattern of surface decoration with PEG (two copies of PEG-20,000 versus six copies of PEG 5K per tetramer) has some role to play in the modulation of vasoactivity. The increase in the viscosity and colloidal oncotic pressure induced by six copies of PEG5K is more efficient in the modulation of the 'pressor effect' than that by two copies of PEG 20K. In the present study PEG 5K chains were conjugated to Hb using a chemistry that is distinct from the 'amidination chemistry' used in the thiolation mediated, maleimide chemistry based PEGylation developed earlier (19, 23).

In designing and developing the thiolation mediated, maleimide chemistry based PEGylation, an approach was also developed for functionalizing PEG-chains with a desired functional group, maleimide moiety through a one step process. This one step functionalizing process is expected to reduce the handling of PEG and hence should reduce the level of peroxy ethers in the functionalized PEG, a limitation of many functionalized PEGs that are currently available. The application of PEGylated Hbs as potential Hb based oxygen carriers would involve the use of significantly larger dosage of this PEGylated protein as compared to the other therapeutic PEGylated proteins. As described herein, the one step functionalizing approach was extended to generate a new class of PEG-reagents, isothiocyanato-phenyl-carbamate of PEG for PEGylation of proteins. The PEGylation of Hb with this reagent that involves the 'isothiocyanate chemistry' will generate a PEG-Hb conjugate in which the chemistry of conjugation as well as the site selectivity of surface decoration of Hb with PEG-chains will be very distinct as compared to the product generated earlier where the site selectivity is primarily dictated by the 'amidation chemistry'.

The reaction of aryl isothiocyanates with the amino groups of proteins to form thiourea derivatives is the classical chemical reaction of the Edman degradation of proteins in the elucidation of the amino acid sequence of proteins. Alkylisothiocyanates, but not generally the aryl derivatives react, with Cys-93(β) of oxy HbA. Around pH 7.0 the four α-amino groups of HbA are reactive towards 4-isothiocyanato benzene sulfonic acid both in oxy and deoxy forms. Various diisothiocyanato compounds have been used to introduce intra molecular cross-bridges, these include 2,5, diisothiocyanato benzene sulfonate and 4,4'-diisothiocyana-tostilbene-2,2'-disulfonate. This 'aryl isothiocyanato chemistry' is designed to translate the site selectivity of this chemistry to obtain a site specific surface decoration of Hb by PEG.

The coupling of the isothiocyanato phenyl isocyanate with PEG appears to proceed smoothly and with better efficiency than the coupling of maleimido phenyl isocyanate. The one-step coupling reaction minimizes the handling of the PEG through synthetic steps. Accordingly, the commercial preparation of monomethoxy PEG, that invariably contain some amounts of peroxy ethers, could be subjected to reduce the peroxy ethers and then subjected to the functionalizing step to eliminate the peroxy ethers in the final functionalized PEG.

The reaction of isothiocyanato phenyl PEG with Hb has been optimized to generate a product that exhibits a hydrodynamic volume comparable to that of the hexaPEGylated Hb that has been isolated previously by the thiolation mediated maleimide chemistry based PEGylation, (SP-PEG5K)$_6$-Hb. The ion exchange chromatography of the sample has demonstrated that the unchromatographed product is heterogeneous even though the size exclusion chromatographic profiles appear to be symmetrical. The unfractionated product carries smaller amounts of tetra and diPEGylated Hb. Component B, which has been isolated as the most heavily PEGylated Hb, also elutes with a peak position corresponding to the (SP-PEG5K)$_6$-Hb, and the primary difference between the product obtained after chromatography and the unfractionated material is the peak width of the SEC-pattern of the two. Component B has a smaller peak width reflecting increased homogeneity of the material. The isoelectric focusing pattern of this material reflects the homogeneity based on the overall surface net charge of the molecule.

The RPHPLC of the (TCP-PEG5K)$_6$-Hb obtained after the ion exchange chromatography suggests this material still lacks molecular homogeneity. This is confirmed by the identification of the sites of PEGylation. It is interesting to note that Val-1(β) and Lys-11(α) of Hb are almost completely PEGylated in this PEG-Hb conjugate. The higher reactivity of α-amino group of Val-1(β) as opposed to that of Val-1(α), and significantly higher reactivity of Lys-11(α) relative to the α-amino group Val-1(α) is distinct from the reactivity of the amino groups of Hb towards the aryl iso-thiocyanates. This reflects either the inaccessibility and/or altered reactivity of the α- and/or the ε-amino groups of Hb for the PEG reagent. It may be noted that when Hb is reacted with 20 mM ITP-PEG5K, one is modifying the macroenvironment of Hb with 20 mM PEG 5K. Accordingly, the conformation of oxy Hb modified by PEG reagent may be very different than the conformation of oxy Hb in the absence of 20 mM PEG5K.

The Cys-93 (β) of the new PEG-Hb conjugate remains reactive towards dithiopyridine, i.e. it is not derivatized during the PEGylation. The thiol group of (TCP-PEG5K)$_6$-Hb appears to be reacting at slightly faster rate than that of HbA itself. However, the oxygen affinity of (TCP-PEG5K)$_6$-Hb is comparable to that of (SP-PEG5K)$_6$-Hb. It was suggested earlier that the high oxygen affinity of (SP-PEG5K)$_6$-Hb is primarily a consequence of the PEGylation of the thiol group of Cys-93(β), and the PEGylation of the thiolated Lys residues appears to have a limited influence on the oxygen affinity of the molecule. Earlier studies have shown that the modification of Hb with simple aryl isothiocyanates reduces the oxygen affinity of Hb. The high oxygen affinity of (TCP-PEG5K)$_6$-Hb suggests that the surface decoration of Hb with PEG-chains by itself has a high oxygen affinity inducing effect. However, such an effect was masked in the studies of (SP-PEG5K)$_6$-Hb as a result of the increased oxygen affinity of (SP-PEG5K)$_2$-Hb, a PEGylated Hb that is site specifically PEGylated at Cys-93(β). The molecular basis of the high oxygen affinity of Hb resulting from the surface decoration with PEG is not apparent at this stage.

The tryptic peptide mapping studies have established that in the new PEG-Hb conjugate, the α-amino group of Val-1 (β) and the ε-amino group of Lys-11(α) are PEGylated almost completely and this accounts for four of the six copies of PEG5K chains present in this new PEG-Hb adduct. The remaining two copies of the PEG-5K chains are distributed over a number of surface amino groups, α-amino group of Val-1 (α) and six other ε-amino groups, those of Lys-16(α), Lys-40(α), Lys-61/90 (α), Lys-82(β) and of Lys-95(β) (the amounts of modification of these amino groups is in the range of 10 to 25%). The results of tryptic peptide mapping, on quantitation gives a value of an average of six PEG5K-chains per tetramer. Thus the average number of PEG-chains in this new PEG-Hb conjugate (i.e. six copies per tetramer) is consistent with its iso-hydrodynamic volume with the hexa PEGylated Hb generated by the thiolation mediated, maleimide chemistry based PEGylation.

Figure 17:
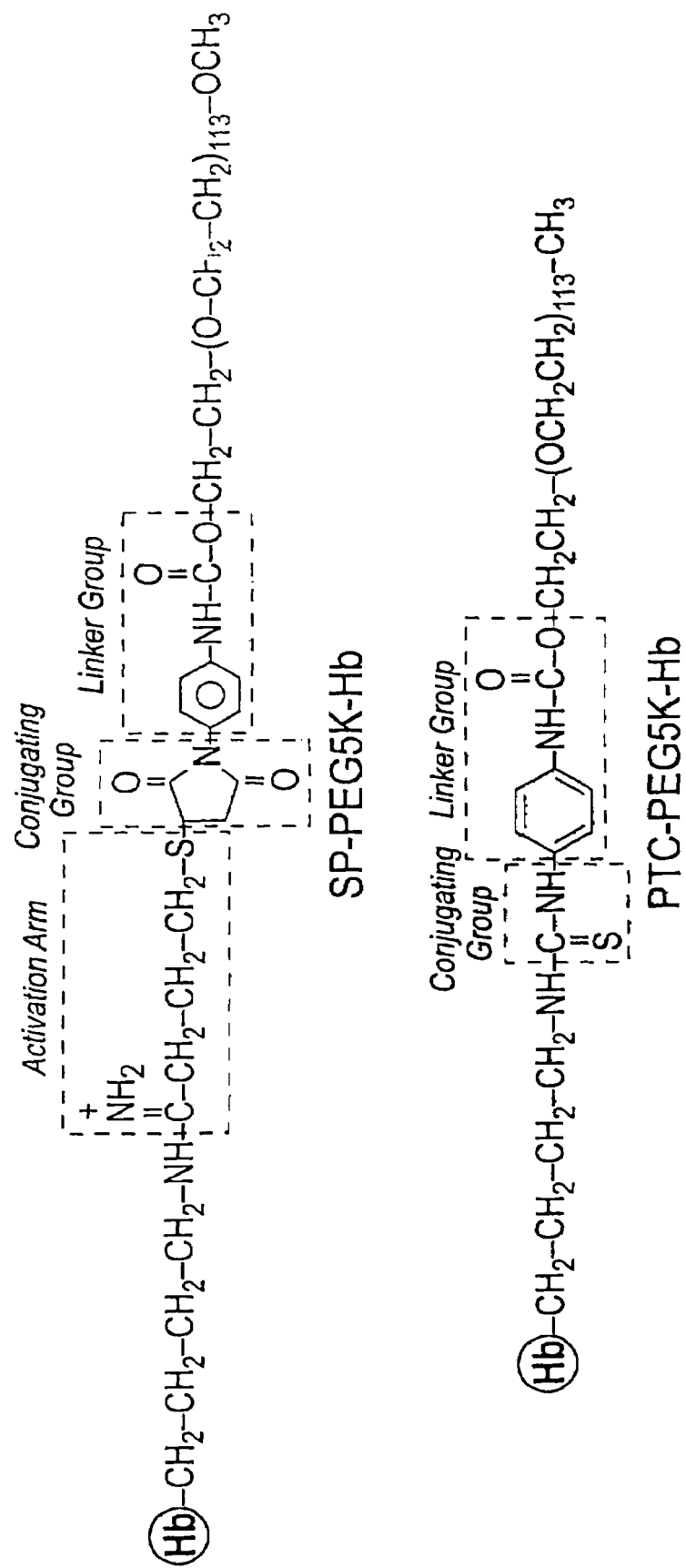
FIG. 17. Comparison of the chemistry of the linkage of PEG-chains to Hb in (SP-PEG5K)$_6$-Hb and (TCP-PEG5K)$_6$-Hb.

The molecular radius of new PEG-Hb conjugate, (TCP-PEG5K)$_6$-Hb is however smaller than that of the hexaPEGylated Hb isolated previously. The hexaPEGylated Hb generated previously carries a 'butyrimidyl extension arm' between the ε-amino groups and the succinimido phenyl PEG5K chains introduced on the Lys residues through the thiolation mediated PEGylation protocol developed earlier. This can place the PEG shell at least 10 AÅ away from the ε-amino groups to which the PEG-chains are linked. On the other hand, the PEG-chains of the new PEG-Hb conjugate are linked to the amino groups directly without the intervening extension arm (FIG. 17). The lower radius of the new PEG-Hb conjugate may be a direct consequence of the lack of this extension arm. The similar isohydrodynamic volume of (SP-PEG5K)$_6$-Hb and (TCP-PEG5K)$_6$-Hb may be a reflection of the different degrees of the compressibility of the PEG-shells of the two proteins during the pressure induced flow.

The viscosity of (TCP-PEG5K)$_6$-Hb is slightly higher than that of (SP-PEG5K)$_6$-Hb. On the other hand the colloidal oncotic pressure of (TCP-PEG5K)$_6$-Hb is significantly higher than that of (SP-PEG5K)$_6$-Hb at all the protein concentrations studied. Thus, apparently, either the chemistry of the conjugation or the presence/absence of the extension arm, or both together, can influence the colloidal oncotic pressure that can be endowed to Hb at a given level of PEGylation with PEG5K.

The top load experiments in hamsters have confirmed that the surface decoration of Hb with six copies of PEG5K chains by the isothiocyanate chemistry attenuates the influence of Hb on the pressor effect and keeps the capillaries well perfused.

The specific advantages of thiolation mediated meleimide chemistry based protocol for PEGylation using Maleidophenyl carbamate of PEG-5000 are: (i) The rigid phenyl linker of the PEG-reagent appears to have a directing influence with respect to Hb modification. (ii) The maleimide chemistry gives a high sulfhydryl specificity, and the maliedophenyl moiety has a good half life. (iii) Iminothiolane mediated thiolation of the ε-amino groups of surface Lys residues, preserves the original positive charge at the modification site. (iv) Surface decoration of Hb by this approach shows considerable promise as a blood substitute.

The advantages of the new phenylisothiocyanate chemistry based PEGylation reaction disclosed herein are: (i) The new reagent has conserved the phenyl group that appears to afford a directing influence on the Hb modification. (ii) The reactive group has a significantly higher half-life compared to the phenyl maleimide moiety. (iii) The thiolation step is not needed, since the functional group of the reagent reacts directly with the amino groups of the proteins. (iv) The closer proximity of the phenyl carbamate moiety to the protein surface (relative to that in the thiolation mediated PEGylation reaction) may provide a better surface coverage of the Hb molecule, an aspect suggested to be one of the factors that facilitates the neutralization of the vasoactivity of acellular Hb. (vi) Cys-93(β), a oxy-deoxy conformation sensitive site of the molecule, is not modified by the aryl isothiocyanate reaction.

One major difference with respect to thiolation mediated, maleimide chemistry based PEGylation is that the charge at the modification site is lost in the reaction of isothiocyanate with the amino groups. Since the PEGylated bovine Hb, modified at its amino groups through amide linkage is also vasoinactive, the loss of the charge occurring on reaction of isothiocyanate with Hb is unlikely to have any significant influence on the vasoactivity of the PEGylated Hb.

As described herein, a comparison has been made of isohydrodynamic volume hexaPEGylated human Hbs generated using four different chemistries: (i) thiolation mediated maleimide chemistry based PEGylation; (ii) reductive alkylation based PEGylation; (iii) thiocarbamoylation based PEGylation; and (iv) acylation chemistry based PEGylation. The hydrodynamic volume and the molecular radius of these PEGylated Hbs revealed a direct correlation between the enhancement in the molecular volume of Hb that is accomplished through PEGylation and the PEG-mass conjugated to Hb. However, the chemistry of conjugation did not reveal any significant influence on these properties.

On the other hand, the chemistry of conjugation appears to have a noticeable influence on the viscosity of Hb, and the influence does not appear to be related to whether or not the charge at the site of PEGylation is altered. The conjugation chemistry that does not alter the surface charge of the protein at the site of PEGylation (conservative PEGylation) increases the viscosity of the PEGylated Hb much less as compared to that in which the charge at the site of PEGylation is neutralized (non-conservative PEGylation). Besides, it should be noted that in the conservative PEGylation protocols the linkage endows a significant flexibility to the PEG chains conjugated to Hb. On the other hand, in the non-conservative PEGylation protocol, the conjugating group imposes a degree of rigidity to the PEG-chains achieved either through the isopeptide linkage or through the thiocarbamoyl phenyl linkage. Thus it appears that neutralization of the charge at the site of conjugation of the PEG-chain and/or the rigidity/flexibility at the conjugating group at the PEGylation site can influence the viscosity of the PEGylated Hb.

Neutralization of the positive charge at the site of conjugation is expected to influence the hydration shell of the Hb molecule. The perturbation and/or the rearrangement of the hydration shell of Hb depending on whether the positive charge of the amino group at the site of PEGylation has been neutralized or not, and further modification of the perturbed hydration shell by the rigidity of the conjugating linkage that restricts the flexibility of the PEG-chain (i.e. structure of the PEG-shell), are likely to be the molecular factors influencing the colligative properties of the PEGylated Hbs.

Unlike the viscosity, the colloidal osmotic pressure of the PEGylated Hbs is strongly influenced by the chemistry of conjugation. Although all the four PEGylated Hbs exhibit similar molecular radius, and similar hydrodynamic volume, their colloidal osmotic pressures are distinct. The two PEGylated Hbs generated by non-conservative PEGylation, TCP-PEG-Hb and Propionyl-PEG-Hb exhibited the highest colloidal osmotic pressure. The PEGylated Hbs generated by the conservative PEGylation protocols, namely (SP-PEG5K)$_6$-Hb and Propyl-PEG-Hb, exhibited lower colloidal osmotic pressures. However, unlike the viscosity of the two conservatively PEGylated Hbs which was close to one another, noticeable difference was observed in their colloidal osmotic pressure. The colloidal osmotic pressure of PEGylated Hb prepared by reductive alkylation protocol, Propyl-PEG-Hb, is significantly higher than that of (SP-PEG5K)$_6$-Hb generated by the thiolation mediated maleimide chemistry based PEGylation. The colloidal osmotic pressure of (SP-PEG5K)$_6$-Hb is the lowest of the four PEGylated Hbs studied. A unique difference between the two PEGylated Hbs generated by conservative PEGylation is that (SP-PEG-5K)$_6$-Hb carries an extension arm between the amino group of Hb and the conjugating group. Accordingly, it appears that the presence of the extension arms between the protein and the PEG-chains lowers the propensity of the conjugated PEG-chains to enhance the colloidal osmotic pressure of the protein.

It may be argued that the differences that exist in the viscosity and colloidal osmotic pressure of the four PEGylated Hbs is a consequence of the differences in the site selectivity of PEGylation rather than being a consequence of the chemistry of conjugation. The observation that the site selectivity of PEGylation in Propyl-PEG-Hb and in TCP-PEG-Hb is nearly the same, but their colloidal osmotic pressures are distinct, supports the concept that the chemistry of conjugation rather than the site selectivity of the PEGylation is the molecular factor that dictates the oncotic pressure of the PEG-Hb conjugates. The structures of Propyl-PEG-Hb and Propionyl-PEG-Hb are comparable except for the fact that replacing two hydrogen atoms of the conjugating group of Propyl-PEG-Hb by an oxygen atom generates Propionyl-PEG-5K-Hb. The difference in the viscosity and the colloidal osmotic pressure of the conservatively PEGylated Propyl-PEG-Hb and the nonconservatively PEGylated Propionyl-PEG-Hb can be considered as the support of the hypothesis that neutralization of the positive charge of the amino groups of Hb that are PEGylated is responsible for the higher increases in the solution properties (relative viscosity and colloidal osmotic pressure) induced to Hb as a result of PEGylation.

The viscosity of the PEGylated Hbs generated by the thiocarbamoylation chemistry is comparable to that of the conservative PEGylation protocols, but their colloidal osmotic pressures are very distinct. This implies that the colloidal osmotic pressure of PEGylated Hbs is not a direct correlate of their viscosity. Consistent with this, tetraPEGylated canine Hb generated by the reaction of maleimido phenyl PEG5K exhibits a relative viscosity and colloidal osmotic pressure comparable to that of the hexaPEGylated Hb, (SP-PEG-5K)$_6$-Hb (45). Since the conjugation is at the reactive Cysteine residues, the tetraPEGylated canine Hb lacks the extension arms between the PEG-chain and amino groups present in (SP-PEG-5K)$_6$-Hb. Although the molecular radius of the tetraPEGylated Hb is smaller than that of (SP-PEG-5K)$_6$-Hb, the tetraPEGylated canine Hb is also vasoinactive just as the hexaPEGylated Hb, (SP-PEG5K)$_6$-Hb. Similarly, a hexaPEGylated Hb generated by reductive alkylation using PEG2K-propinaldehyde exhibits a colloidal osmotic pressure close to that of the tetraPEGylated canine Hb.

The finding that the hexaPEGylated Hb, (SP-PEG5K)$_6$-Hb generated by thiolation mediated maleimide chemistry based PEGylation is non-hypertensive supports the hypothesis that engineering solution properties comparable to those of colloid plasma expanders to Hb through PEGylation neutralizes the vasoactivity of Hb. The results of the studies of PEGylated Hb with multiple copies of PEG-5K chains achieved through new and different chemistries described here demonstrate that the molecular volume of the PEG-Hb adduct is a direct correlate of the number of PEG-chains and is not influenced by the conjugation chemistry. On the other hand, the viscosity and the oncotic pressure of these PEGylated Hbs is not a direct correlate of the PEG-mass conjugated and the chemistry of conjugation plays a significant role in dictating these solution properties of the PEG-Hb conjugates. Accordingly, novel PEGylated Hbs with customized physical and solution properties can be designed and generated to delineate the interplay of the molecular size, viscosity and colloidal osmotic pressure of PEGylated Hb in producing non-hypertensive Hb (oxygen carrying plasma expanders).

All publications mentioned herein are hereby incorporated in their entirety into the subject application. While the foregoing invention has been described in some detail for purposes of clarity and understanding, it will be appreciated by one skilled in the art, from a reading of the disclosure, that various changes in form and detail can be made without departing from the true scope of the invention in the appended claims.

REFERENCES

1. Winslow, R. M. 1999. New Transfusion Strategies: red Cell Substitutes. *Ann. Rev. Med* 50:337.

2. Amberson W., Jennigs J., and Rhodes C. 1949. Clinical experience with hemoglobin-saline solutions. *J. Appl. Physiol.* 1:469.

3. Savitsky J., Doczi J., and Black J. 1978. A clinical safety trial of stroma-free hemoglobin. *Clin. Pharmacol. Therap.* 23:73.

4. Sloan E. P., Koenigsberg M., and Gens D. 1999. Diaspirin crosslinked hemoglobin (DCL-Hb) in the treatment of severe traumatic hemorrhagic shock. A randomized controlled efficacy trial. *J. Amer. Med Assoc.* 282:1857.

5. Saxena R., Wijnhoud A. D., and Carton H. 1999. Controlled safety study of a hemoglobin-based oxygen carrier, DCLHb, in acute ischemic stroke. *Stroke* 30:993.

6. Hess, J. R., V. W. Macdonald, and W. W. Brinkley. 1993. Systemic and pulmonary hypertension after resuscitation with cell free hemoglobin. *J. Appl. Physiol.* 74:1769.

7. Thomson, A., A. E. McGarry, C. R. Valeri, and W. Lieberthal. 1994. Stroma-free hemoglobin increases blood pressure and GFR in the hypotensive rat: role of nitric oxide. *J. Appl. Physiol.* 77:2348.

8. Muldoon, S. M., M. A. Ledvina, J. L. Hart, and Macdonald V W. 1996. Hemoglobin-induced contraction of pig pulmonary veins. *J. Lab. Clin. Med.* 128:579.

9. Motterlini, R., K. D. Vandegriff, and R. M. Winslow. 1996. Hemoglobin-nitric oxide interactions and its implications. *Transfusion Medicine Rev.* 10:77.

10. Doherty D. H., Doyle M. P., and Curry S. R. 1998. Rate of reaction with nitric oxide determines the hypertensive effect of cell-free hemoglobin. *Nature Biotechnol.* 16:672.

11. Dou Y., Maillett D. H., Eich R. F., and Olson J. S. 2002. Myoglobin as a model system for designing heme protein based blood substitutes. *Biophysical Chemistry* 98:127.

12. Furchgott, R. 1984. The role of endothelium in the responses of vascular smooth muscle to drugs. *Ann. Rev. Pharmacol.* 24:175.

13. Kilboum, R., J. Ghislaine, B. Cashon, J. DeAngelo, and J. Bonaventura. 1994. Cell-free hemoglobin reverses the endotoxin mediated hyporesponsivity of rat aortic rings to $\alpha$-adrenergic agents. *Biochem. Biophys. Res. Commun.* 199:155.

14. Eich R. F., Li T., and Lemon D. D. 1996. Mechanism of NO-induced oxidation of myoglobin and hemoglobin. *Biochemistry* 35:6976.

15. Macdonald V. W. and Motterlini R. 1994. Vasoconstrictor effects in isolated rabbit heart perfused with bis-(3, 5-dibromosalicyl)fumarate crosslinked hemoglobin. *Artificial Cells, Blood Substitutes and Immobilization Biotechnology* 22:565.

16. Rohlfs, R. J., E. Bruner, A. Chiu, A. Gonzales, M. L. Gonzales, M. D. Magde, K. D. Vandegriff, and R. M. Winslow. 1998. Arterial blood pressure responses to cell-free hemoglobin solutions and the reaction with nitric oxide. *J. Biol. Chem.* 273:12128.

17. Winslow, R. M., A. Gonzales, M. L. Gonzales, M. D. Magde, M. McCarthy, R. J. Rohlfs, and K. D. Vandegriff. 1998. Vascular resistance and efficacy of red cell substitutes in a rat hemorrhage model. *J. Appl. Physiol.* 85:993.

18. Vandegriff, K. D., M. McCarthy, R. J. Rohlfs, and Winslow R M. 1997. Colloid osmotic properties of modified hemoglobins: chemically cross-linked versus polyehtylene glycol surface-conjugated. *Biophysical Chemistry* 69:23.

19. Acharya, A. S., Manjula, B. N, and Smith, P. K. Hemoglobin crosslinkers. U.S. Pat. No. 5,585,484, issued Dec. 17, 1996.

20. Manjula, B. N., A. Malavalli, Smith P. K., N.-L. Chan, A. Amone, J. M. Friedman, and A. S. Acharya. 2000. Cys-93-$\beta\beta$-succinimidophenyl polyethylene glycol 2000 hemoglobin A. *J. Biol. Chem.* 275:5527.

21. Traut R. R., Bollen A., Sun T. T., Hershey J. W. B., Sundberg J., and Pierce L. R. 1973. Methyl 4-mercaptobutyrimidate as a cleavable crosslinking reagent and its application to the *Escherichia coli* 30S ribosome. *Biochemistry* 12:3266.

22. Lambert J. R., Pierce L. R., and Traut R. R. 1978. Addition of sulfhydryl groups to *Escherchia coli* ribosomes by protein modification with 2-iminothiolane (methyl 4-mercaptobutyrimidate). *Biochemistry* 17:5399.

23. Acharya A. S., Intaglietta M., Tsai A. G., Malavalli A, Vandegriff K., Winslow R. M., Smith P. K., Friedman J. M., and Manjula B. N. 2003. (PEG5K)$_6$-Hb: A non-hypertensive hemoglobin molecule generated by conservative PEGylation. *Abstract, The 9$^{th}$ International Symposium on Blood Substitutes, Tokyo, Japan*, March 2003.

24. Manjula B. N. and Acharya A. S. 2003. Purification and Molecular Analysis of Hemoglobin by High-Performance Liquid Chromatography. In *Methods in Molecular Medicine: Hemoglobin Disorders: Molecular Methods and Protocols*. Ed. Nagel R. L. Humana Press, Totowa, N.J. Vol. 82, p 31.

25. Manjula B. N., Tsai A., Upadhya R., Perumalsamy K., Smith P. K., Malavalli A, Vandegriff K. D., Winslow R. M., Intaglietta M., Prabhakaran M., Friedman J. M., and Acharya A. S. 2003. Site-specific PEGylation of hemoglobin at Cys-93($\beta$): Correlation between the colligative properties of the PEGylated protein and the length of the conjugated PEG chain. *Bioconjugate Chem.* 14:464.

26. Plateau, P. and M. Gueron. 1982. Exchangeable proton NMR without base-line distorsion, using new strong-pulse sequences. *J. Am. Chem. Soc.* 104:7310.

27. Mirhashemi, S., G. A. Breit, R. H. Chavez, and M. Intaglietta. 1988. Effects of hemodilution on skin microcirculation. *Am. J. Physiol. (Heart Circ. Physiol.* 23) 254: H411.

28. Tsai, A., H. Kerger, and M. Intaglietta. 1996. Microvascular oxygen distribution: Effects due to free hemoglobin in plasma. In Blood Substitutes. New Challenges. R. M. Winslow, K. D. Vandegriff, and M. Intaglietta, editors. Birkhauser, Boston. 124–131.

29. Tsai, A. G., B. Friesenecker, M. McCarthy, H. Sakai, and M. Intaglietta. 1998. Plasma viscosity regulates capillary perfusion during extreme hemodilution in hamster skinfold model. *Am. J. Physiol.* 275:H2170.

30. Kerger, H., D. J. Saltzman, M. D. Menger, K. Messmer, and M. Intaglietta. 1996. Systemic and subcutaneous microvascular $PO_2$ dissociation during 4-h hemorrhagic shock in conscious hamsters. *Am. J. Physiol.* 270:H827.

31. Tsai, A. G., B. Friesenecker, and M. Intaglietta. 1995. Capillary flow impairment and functional capillary density. *Int. J. Microcirc. Clin. Exp.* 15:238.

32. Ho, C. 1992. Proton nuclear magnetic resonance studies on hemoglobin: cooperative interactions and partially ligated intermediates. *Adv. Prot. Chem.* 43:153.

33. Fung, L. W. M. and C. Ho. 1975. Proton nuclear magnetic resonance study of the quaternary structure of human hemoglobins in water. *Biochemistry* 14:2526.

34. Acharya V. N., Manjula B. N., Malavalli A, Vandegriff K., Friedman J. M., and Acharya A. S. 2002. Correlation of the increase in hydrodynamic volume and viscosity of hemoglobin as a function of PEGylation with PEG5000. *Biophys. J* 82:446a. (Abstract).

35. King, T. P., Y. Li, and L. Kochoumian. 1978. Preparation of protein conjugates via intermolecular disulfide bond formation. *Biochemistry* 17:1499.

36. Meunier, L., S. Bourgerie, R. Mayer, A.-C. Roche, and M. Monsigny. 1999. Optimized conditions to couple two water-soluble biomolecules through alkylamine thiolation and thioetherification. *Bioconjugate Chem.* 10:206.

37. McCall, M. J., H. Diril, and C. F. Meares. 1990. Simplified method for conjugating macrocyclic bifunctional chelating agents to antibodies via 2-iminothiolane. *Bioconjugate Chem.* 1:222.

38. Karacay, H., R. M. Sharkey, S. S. Govindan, W. J. McBride, D. m. Goldenberg, H. J. Hansen, and G. L. Griffiths. 1997. Development of a streptavidin-anti-carcinoembryonic antigen antibody, radiolabeled biotin pretargeting method for radioimmunotherapy of colorectal cancer. Reagent development. *Bioconjugate Chem.* 8:585.

39. Chapman, A. P., P. Antoniw, M. Spitali, S. West, S. Stephens, and D. J. King. 1999. Therapeutic antibody fragments with prolonged in vivo half-lives. *Nature Biotechnol.* 17:780.

40. Lasch, J., G. Niedermann, A. A. Bogdanov, and V. P. Torchilin. 1987. Thiolation of prefered liposomes with iminothiolane. *FEBS Letters* 214:13.

41. Singh, R., L. Kats, W. A. Blattler, and J. M. Lambert. 1996. Formation of N-substituted 2-iminothiolanes when amino groups in proteins and peptides are modified by 2-iminothiolane. *Anal. Biochem* 236:114.

42. Khan, I, D. Dansker, U. Samuni, A. J. Friedman, C. Bonaventura, Manjula B. N., Acharya A. S., and Friedman J. M. 2001. Cys-93(β) modified hemoglobin: Kinetic and conformational consequences. *Biochemistry* 40:7581.

43. Juszczak, L. J., Manjula B. N., C. Bonaventura, Acharya A. S., and Friedman J. M. 2002. UV Resonance Raman study of β93-modified hemoglobin A: Chemical modifier-specific effects and added influences of attached poly(ethylene glycol) chains. *Biochemistry* 41:376.

44. Vandegriff K. D., Malavalli A, Wooldridge J., Lohman J., and Winslow R. M. 2003. MP4, a new nonvasoactive PEG-Hb conjugate. *Transfusion* 43:509.

45. Acharya, V., Tsai, A. G., Intaglietta, M., Kanika, N. D., Prabhakaran, M., Manjula, B. N. and Acharya, A. S. *Abstract, ASBMB Annual Meeting and 8th IUBMB Conference*, Boston, Mass. June 2004.

46. Acharya, S. A. and Manjula, B. N. Size Enhanced Hemoglobins: Surface Decoration and Crosslinking of the Protein with Polyoxy Alkylene Glycols. U.S. Patent Application Publication No. U.S. 2004/0002443 A1, published Jan. 1, 2004.

What is claimed is:

1. A PEGgylated hemoglobin comprising a thiocarbamoyl-phenyl-carbamate of polyethylene glycol (PEG) attached to hemoglobin.

2. The PEGylated hemoglobin of claim 1, wherein the thiocarbamoyl-phenyl-polyethylene glycol (PEG) is attached to an α-amino group or to an ε-amino group of the hemoglobin.

3. The PEGylated hemoglobin of claim 1, comprising a PEG with a molecular weight of 200–40,000 daltons.

4. The PEGylated hemoglobin of claim 1, wherein the polyethylene glycol (PEG) has a molecular weight of 3,000–5,000 daltons.

5. The PEGylated hemoglobin of claim 1, wherein the polyethylene glycol (PEG) has a molecular weight of 5,000 daltons.

6. The PEGylated hemoglobin of claim 1, comprising the structure shown in the bottom of FIG. 1 or in the bottom of FIG. 17.

7. The PEGylated hemoglobin of claim 1, wherein two to eight thiocarbamoyl-phenyl-polyethylene glycol (PEG) groups are attached to the hemoglobin.

8. The PEGylated hemoglobin of claim 1, wherein six thiocarbamoyl-phenyl-polyethylene glycol (PEG) groups are attached to the hemoglobin.

9. The PEGylated hemoglobin of claim 1, having a radius of at least 5 nm.

10. The PEGylated hemoglobin of claim 1, wherein the PEGylated hemoglobin has a viscosity that is at least 3 times greater than non-PEGylated hemoglobin.

11. The PEGylated hemoglobin of claim 1, wherein the PEGylated hemoglobin has a colloidal osmotic pressure that is at least 4 times greater than non-PEGylated hemoglobin.

12. A composition comprising the PEGylated hemoglobin of claim 1 and a pharmaceutically acceptable carrier.

13. A blood substitute comprising the PEGylated hemoglobin of claim 1.

* * * * *